United States Patent [19]

Myojo et al.

[11] Patent Number: 5,219,733
[45] Date of Patent: Jun. 15, 1993

[54] PROCESS FOR PREPARING FATTY ACID ESTERS

[75] Inventors: Katsunori Myojo; Youichi Matsufune, both of Kakogawa; Shiro Yoshikawa, Ashiya, all of Japan

[73] Assignee: Yoshikawa Oil & Fat Co., Ltd., Japan

[21] Appl. No.: 563,895

[22] Filed: Aug. 7, 1990

Related U.S. Application Data

[63] Continuation of Ser. No. 836,362, Mar. 5, 1986, abandoned.

[30] Foreign Application Priority Data

Mar. 6, 1985 [JP] Japan ................................. 60-45128
Aug. 29, 1985 [JP] Japan ............................... 60-190543
Jan. 16, 1986 [JP] Japan ................................... 61-7732

[51] Int. Cl.$^5$ .................... C12P 33/00; C12P 7/62; C12P 7/64; C12N 9/20
[52] U.S. Cl. ........................ 435/52; 435/135; 435/134; 435/198; 435/176; 435/177; 435/474; 435/921; 435/939; 435/913; 435/196; 435/197
[58] Field of Search ............... 435/135, 134, 52, 196, 435/197, 198, 176, 177, 913, 874, 921, 183, 939

[56] References Cited

U.S. PATENT DOCUMENTS

| | | | |
|---|---|---|---|
| 3,869,349 | 3/1975 | Goodhue | 435/225 |
| 4,275,011 | 6/1981 | Tanaka et al. | 435/134 |
| 4,275,081 | 6/1981 | Coleman et al. | 435/134 |
| 4,360,596 | 11/1982 | Beaucamp et al. | 435/197 |
| 4,614,718 | 9/1986 | Seino et al. | 435/135 |

FOREIGN PATENT DOCUMENTS 0120285 3/1984 European Pat. Off. ............ 435/134

OTHER PUBLICATIONS

Okumura et al, *Biochim. Biophys. Acta*, vol. 575 (1979) pp. 156–165.
Iwai et al. *Agric. Biol. Chem.* vol. 44 (11) pp. 2731–2732, 1980.
Hog et al. *JAOCS*, vol. 61 (4) 1984, pp. 776–781.
Rudd et al in "Lipases", 1984, Borgstrom et al ed. Elsevier., pp. 185–204.
Iwai et al in "Lipases", 1984, Borgstrom et al, ed. Elsevier, pp. 443–469.

*Primary Examiner*—Irene Marx
*Attorney, Agent, or Firm*—Armstrong, Westerman, Hattori, McLeland & Naughton

[57] ABSTRACT

A process for reacting
(1) a component selected from the group consisting of sterols and branched aliphatic primary or secondary alcohols having 14 to 32 carbon atoms, and
(2) a component selected from the group consisting of fatty acids and fatty acid esters in contact with an enzyme selected from the group consisting of lipase and cholesterol esterase or with the selected enzyme in an immobilized form, in a system selected from the group consisting of an aqueous medium and water-containing organic solvent to prepare a fatty acid ester of the component (1).

57 Claims, 11 Drawing Sheets

PROCESS FOR PREPARING FATTY ACID ESTERS

This application is a continuation of application Ser. No. 836,362 filed Mar. 5, 1986, abandoned.

The present invention relates to a process for preparing sterol esters or specific aliphatic alcohol esters of fatty acids with use of an enzyme.

Esters of sterols with fatty acids are widely used in various fields, for example, as cholestric liquid crystals (see Unexamined Japanese Patent Publication SHO 52-24992) and hydrophilic base materials for pharmaceuticals and cosmetics (see Unexamined Japanese Patent Publications SHO 52-41215 and SHO 52-79030).

Such fatty acid-sterol esters and the like have heretofore been prepared solely by organic synthetic processes, which generally employ severe reaction conditions, involve a side reaction and require complex procedures for the reaction and for the subsequent isolation and purification of the desired product. The hydroxyl group of sterols is secondary, is positioned close to the steroid skeleton and therefore exhibits reduced reactivity. For preparing fatty acid esters by reacting fatty acids with sterols, it is necessary to react the starting materials at a high temperature for a long period of time using an acid catalyst, or to convert the fatty acid to an acid anhydride or acid halide first before esterification. Further when the sterol material is trimethylsterol having two methyl groups at the 4-position of the steroid skeleton, one methyl at the 14-position and a hydroxyl group at the 3-position, the compound has still lower reactivity due to the steric hindrance of the two methyl groups at the 4-position and is difficult to esterify with a fatty acid unless the acid is converted to an acid halide. However, sterol esters which are useful for various applications are generally long-chain fatty acid esters, and long-chain fatty acid halides serving as materials for preparating such esters are usually difficult to obtain, need to be prepared specifically by a complex process and are very expensive. In addition, these fatty acid halides are generally unstable and prone to decomposition in the presence of moisture, are likely to give a stimulating corrosive by-product during reaction and require a special reactor or the like. For preparing fatty acid esters by reacting sterols with fatty acid esters, the materials need to be reacted at a high temperature for a prolonged period of time in the presence of an inorganic catalyst such as sodium alcoholate.

Such organic chemical processes have the drawback of being low in reaction selectivity and entailing deterioration of the substrate and consumption of a large amount of energy due to the use of severe conditions. Furthermore, they have the serious drawback of necessitating removal of the catalyst and being low in reaction yield.

In recent years, research is under way on processes for synthesizing glycerides and terpene esters by the reverse reaction of hydrolases such as lipase instead of resorting to organic synthesis. Nevertheless, nothing has been reported on processes in which enzymes are used for synthesizing esters from fatty acids or fatty acid esters and sterols or branched aliphatic primary or secondary alcohols having 14 to 32 carbon atoms.

Generally, enzyme reactions are substrate-specific, and it is impossible to predict progress of an enzymatic synthesis reaction if a different compound is used as the contemplated substrate. It is also known that the equilibrium of a synthesis reaction with lipase usually predominantly proceeds reversely. Even the above-mentioned processes investigated in reacent years require special means such as the reduction of the amount of water in the reaction system to the greatest possible extent so as to shift the equilibrium toward synthesis. Use of such an expedient results in a decreased reaction velocity, usually giving the desired ester in a reduced yield.

An object of the present invention is to provide a process for preparing a desired ester under moderate conditions, using an enzyme but without resorting to organic synthesis involving disadvantages such as severe reaction conditions.

Another object of the present invention is to provide a process for preparing the desired ester economically with ease and in a high yield.

Still another object of the present invention is to provide a process for preparing the desired ester by a continuous or semicontinuous synthesis reaction using an enzyme repeatedly.

These and other objects of the present invention will become apparent from the following description.

Figure 1:
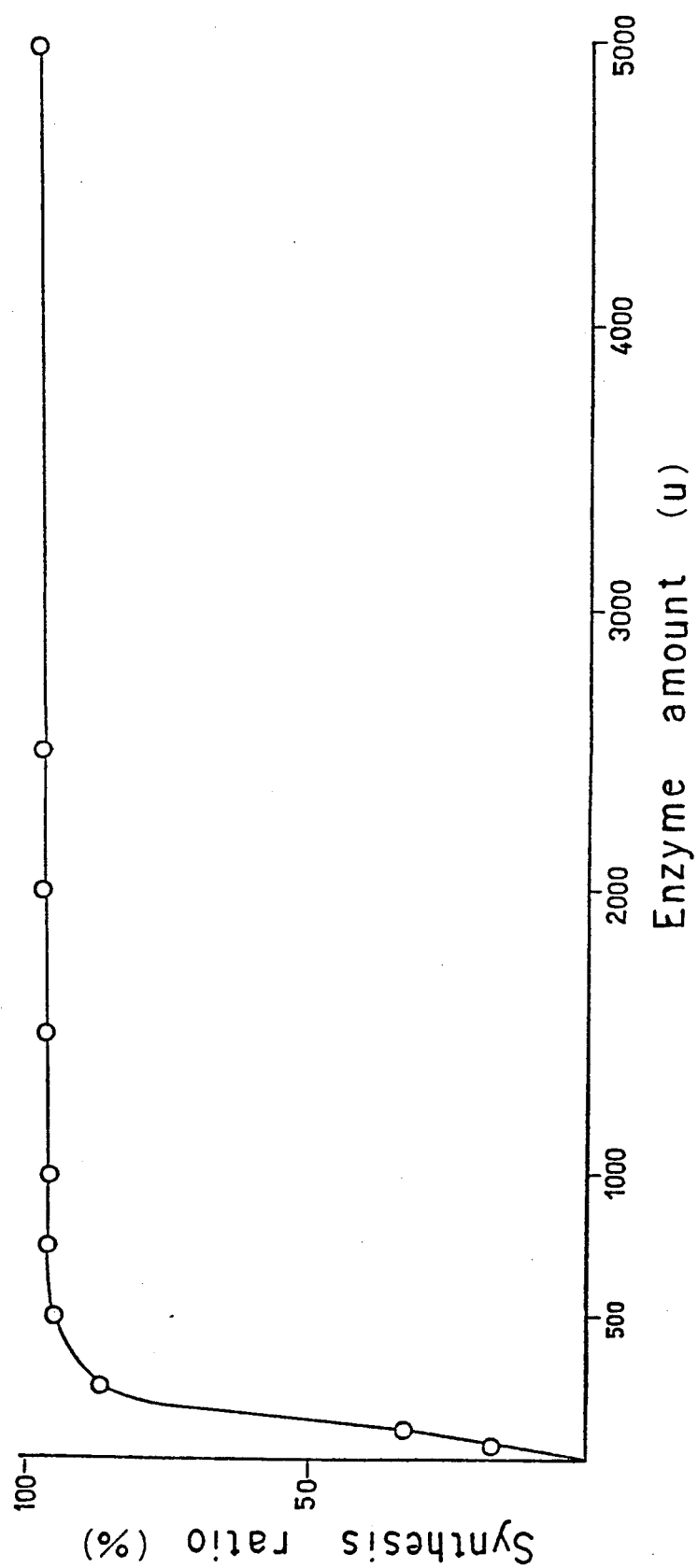
FIG. 1 is a graph of the results obtained from Example 7, showing the correlation between the enzyme concentration and the synthesis ratio of the ester.

The present invention provides a process for reaction (1) a component selected from the group consisting of sterols and branched aliphatic primary or secondary alcohols having 14 to 32 carbon atoms, and (2) a component selected from the group consisting of fatty acids and fatty acid esters in contact with an enzyme selected from the group consisting of lipase and cholesterol esterase or the selected enzyme in an immobilized form, in a system selected from the group consisting of an aqueous medium and water-containing organic solvent to prepare a fatty acid ester of the component (1).

The process of the present invention affords the desired ester easily in a high yield under very moderate conditions with reduced energy consumption by using an enzyme, without severe reaction conditions, separate preparation of starting materials and special reactor or the like which are needed for conventional organic synthesis processes and further without involving disadvantages such as poor reaction selectivity, degradation of the substrate, use of other catalyst and removal thereof.

Further with the process of the present invention, the reaction can be carried out continuously or semicontinuously by repeatedly using the enzyme, so that the process can be practiced automatically with ease to prepare the desired ester with a great reduction achieved in the amount of labor, manufacturing cost and equipment cost.

Generally in synthesizing glycerides with use of lipase, it is essentially required to reduce the amount of water in the reaction system to the greatest possible extent except a minimum required for the enzyme to exhibit its activity so as to permit the synthesis reaction to proceed favorably, whereas in the presence of a reduced amount of water, the enzyme fails to fully exhibit its activity with a tendency for the reaction velocity to decrease. Nevertheless, the combination of substrates according to the invention permits the synthetic reaction to proceed favorably at a sufficiently high velocity even if the reaction system contains a large amount of water. The present process is therefor especially suited to industrial operation.

The enzyme to be used for the process of the invention is selected from the group consisting of lipase and cholesterol esterase. The term "lipase" refers to an enzyme for catalyzing the stepwise hydrolysis of a glyceride to glycerin and a fatty acid. The term "cholesterol esterase" refers to an enzyme for hydrolyzing the ester of cholesterol and a fatty acid. The lipase and cholesterol esterase are not specifically limited in their origin, but various microorganisms, animals and vegetables can be their origins.

Examples of microorganisms from which lipase is derived are those of the genus Achromobacter such as *Achromobacter iofurgus* and *Achromobacter lipolyticum*, the genus Chromobacterium such as *Chromobacterium viscosum*, the genus Corynebacterium such as *Corynebacterium acnes*, the genus Staphylococcus such as *Staphylococcus aureus*, the genus Aspergillus such as *Aspergillus niger*, the genus Candida such as *Candida cylindracea*, the genus Humicora such as *Humicora lanuginosa*, the genus Penicillium such as *Penicillium caseicolum*, *Penicillium crustosum*, *Penicillium cyclopium* and *Penicillium roqueforti*, the genus Torulopsis such as *Torulopsis ernobii*, the genus Mucor such as *Mucor miehei*, the genus Bacillus such as *Bacillus subtilis*, the genus Thermomyces such as *Thermomyces ibadanensis*, the genus Rhizopus such as *Rhizopus delemar*, the genus Pseudomonas such as *Pseudomonas aeruginosa*, *Pseudomonas fragi* and *Pseudomonas fluorescens*, the genus Alcaligenes such as Alcaligenes sp, etc.

Examples of useful origins from which cholesterol esterase is derived are those of the animal tissues such as pancreas, liver, brain, adrenal gland, testis, ovary, etc. Microorganisms are also preferably usable as the origins. Examples of the microorganisms are those of the genus Pseudomonas such as *Pseudomonas aeruginosa* and *Pseudomonas fluorescens*, the genus Achromobacter such as *Achromobacter delicatulus*, the genus Fusarium, the genus Nocardia, the genus Streptomyces, the genus Candida such as *Candida lipolytica*, *Candida tropicalis*, *Candida intermedia* and *Candida cylindracea*, etc.

A majority of enzymes of such origins are commercially available as purified enzymes. Although these commercial products are usable as they are in this invention, purified commercial products need not always be used. Similarly usable are, for example, cells of microorganism itself capable of producing the contemplated enzyme, a culture of such cells, a crude enzyme solution obtained by treating the culture, a composition containing the enzyme, etc.

The immobilized enzyme to be used for the invention can be any of those prepared by immobilizing the above enzymes to suitable carriers by a usual method. The immobilized enzyme and preparation thereof will be described in detail later.

The sterol to be used as one of the substrates to be subjected to a synthesis reaction using the enzyme or immobilized enzyme is a compound having a steroid skeleton and a hydroxyl group in the molecule. The steroid skeleton is represented by the formula (I)

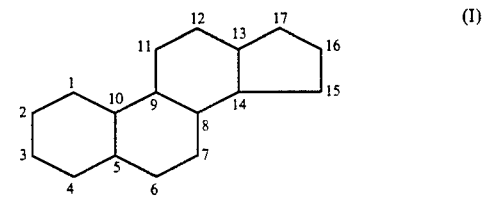

Generally, the hydroxyl group is attached the skeleton. Examples of useful sterols are cholesterol, 7-dehydrocholesterol, β-cholestanol, coprostanol, lathosterol, zymosterol, zymostenol, desmosterol, brassicasterol, ergosterol, campesterol, β-sitosterol, γ-sitosterol, α-spinasterol, stigmasterol, trimethylsterols including lanosterol, dihydrolanosterol, agnosterol and dihydroagnosterol, isocholesterol separated from wool wax as a mixture of such sterols, cycloartenol, etc.

According to the present invention, a branched aliphatic primary or secondary alcohol having 14 to 32 carbon atoms is usable as one of the substrates in place of, or conjointly with, the sterol. Such alcohols may be saturated or unsaturated, and monohydric, dihydric or polyhydric, and can be used in admixture. Examples of such alcohols are as follows.

(I) Branched aliphatic saturated alcohols represented by the formula

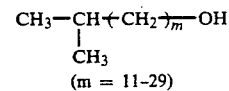

(m = 11–29)

and those represented by the formula

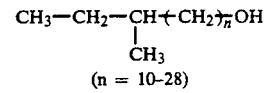

(n = 10–28)

More specific examples of these alcohols are 14-methylhexadecanol-1, 16-methyloctadecanol-1, 18-methylnonadecanol, 18-methyleicosanol, 20-methylheneicosanol, 20-methyldocosanol, 22-methyltricosanol, 22-methyltetracosanol, 24-methylpentacosanol-1, 24-methylhexacosanol and mixtures of such alcohols, e.g., Lanolin alcohol HH (product of Yoshikawa Oil and Fat Co., Ltd.) which is an aliphatic higher alcohol-glycol mixture derived from lanolin alcohols by solvent fractionation, free of sterol and consisting chiefly of branched aliphatic saturated lanolin alcohols having 18 to 32 carbon atoms.

(II) Branched synthetic alcohols such as Hexadecyl alcohol (Esso Standard), NJCOL 160A, 160B, 181A, 200A and 200C (New Japan Chemical), Fine oxocol 1800 (Nissan Chemical Industries, Ltd.), DIADOL 18G (Mitsubishi-Kasei), Octyldodecanol (Henkel International GmbH), etc.

(III) Branched synthetic secondary alcohols including Isotridecyl alcohol (KURARAY CO., LTD.) and those represented by the formula

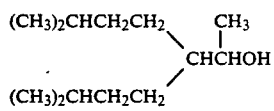

(IV) α,β-Diols represented by the formulae

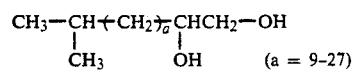

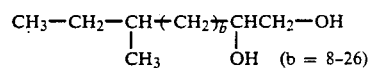

According to the invention, a fatty acid or fatty acid ester is used as the other substrate material.

The fatty acids to be used include saturated straight-chain fatty acids, saturated branched fatty acids, unsaturated fatty acids, hydroxy fatty acids, polycarboxylic acids, etc., these acids having up to 32 carbon atoms.

Examples of useful saturated straight-chain fatty acids are those having an even number of carbon atoms, such as acetic acid, butyric acid, caproic acid, caprylic acid, capric acid, lauric acid, myristic acid, palmitic acid, stearic acid, arachic acid, behenic acid, lignoceric acid, hexacosanoic acid, octacosanoic acid, triacontanoic acid and n-dotriacontanoic acid, and those having an odd number of carbon atoms, such as propionic acid, n-valeric acid, enanthic acid, pelargonic acid, hendecanoic acid, tridecanoic acid, pentadecanoic acid, heptadecanoic acid, nonadecanoic acid, heneicosanoic acid, tricosanoic acid, pentacosanoic acid and heptacosanoic acid.

Examples of useful saturated branched fatty acids are isobutyric acid, isocaproic acid, isocaprylic acid, isocapric acid, isolauric acid, 11-methyldodecanoic acid, isomyristic acid, 13-methyl-tetradecanoic acid, isopalmitic acid, 15-methyl-hexadecanoic acid, isostearic acid, 17-methyloctadecanoic acid, isoarachic acid, 19-methyl-eicosanoic acid, α-ethyl-hexanoic acid, α-hexyldecanoic acid, α-heptylundecanoic acid, 2-decyltetradecanoic acid, 2-undecyltetradecanoic acid, 2-decylpentadecanoic acid, 2-undecylpentadecanoic acid, and Fine oxocol 1800 acid (product of Nissan Chemical Industries, Ltd.) represented by the formula (II)

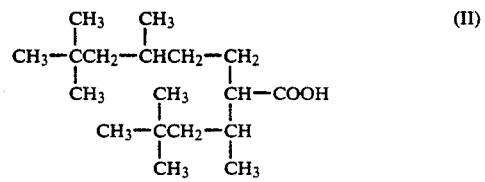

Useful saturated odd-carbon branched fatty acids include anteiso fatty acids terminating with an isobutyl group, such as 6-methyl-octanoic acid, 8-methyl-decanoic acid, 10-methyl-dodecanoic acid, 12-methyl-tetradecanoic acid, 14-methyl-hexadecanoic acid, 16-methyl-octadecanoic acid, 18-methyl-eicosanoic acid, 20-methyl-docosanoic acid, 22-methyl-tetracosanoic acid, 24-methyl-hexacosanoic acid and 26-methyloctacosanoic acid.

Examples of useful unsaturated fatty acids are 4-decenoic acid, caproleic acid, 4-dodecenoic acid, 5-dodecenoic acid, lauroleic acid, 4-tetradecenoic acid, 5-tetradecenoic acid, 9-tetradecenoic acid, palmitoleic acid, 6-octadecenoic acid, oleic acid, 9-octadecenoic acid, 11-octadecenoic acid, 9-eicosenoic acid, cis-11-eicosenoic acid, cetoleic acid, 13-docosenoic acid, 15-tetracosenoic acid, 17-hexacosenoic acid, 6,9,12,15-hexadecatetraenoic acid, linoleic acid, linolenic acid, α-eleostearic acid, β-eleostearic acid, punicic acid, 6,9,12,15-octadecatetraenoic acid, parinaric acid, 5,8,11,14-eicosatetraenoic acid, 5,8,11,14,17-eicosapentaenoic acid, 7,10,13,16,19-docosapentaenoic acid, 4,7,10,13,16,19-docosahexaenoic acid and the like.

Examples of useful hydroxy fatty acids are α-hydroxylauric acid, α-hydroxymyristic acid, α-hydroxypalmitic acid, α-hydroxystearic acid, ω-hydroxylauric acid, α-hydroxyarachic acid, 9-hydroxy-12-octadecenoic acid, ricinoleic acid, α-hydroxybehenic acid, 9-hydroxy-trans-10,12-octadecadienic acid, kamolenic acid, ipurolic acid, 9,10-dihydroxystearic acid, 12-hydroxystearic acid and the like.

Examples of useful polycarboxylic acids are oxalic acid, malonic acid, succinic acid, glutaric acid, adipic acid, pimelic acid, suberic acid, azelaic acid, sebacic acid, D,L-malic acid and the like.

For the reaction of the present invention, these fatty acids can be used singly, or at least two of such acids of the same group or different groups are usable in admixture. When at least two acids are used in combination, lanolin fatty acid, for example, is advantageously usable which is a mixture of saturated straight-chain and branched fatty acids and hydroxy fatty acids.

Fatty acid esters useful as the other substrate material of the invention include glycerin esters of the foregoing fatty acids and esters of these acids with aliphatic alcohols having 1 to 32 carbon atoms, preferably up to 14 carbon atoms. The aliphatic alcohols having 1 to 32 carbon atoms and serving as the alcohol component of these esters may be monohydric or dihydric, and straight-chain or branched. Especially preferable of such alcohols are those having 1 to 6 carbon atoms, such as methyl alcohol, ethyl alcohol, n-propyl alcohol, isopropyl alcohol, n-butyl alcohol, isobutyl alcohol, n-hexyl alcohol and the like.

The glycerin esters of fatty acids may be monoglycerides, diglycerides or triglycerides, or mixtures of such glycerides. Accordingly, fatty acid esters useful as starting materials of the invention include natural and synthetic oils and fats (glycerides), natural and synthetic waxes, etc. Examples of useful natural oils and fats are vegetable oils such as linseed oil, olive oil, cacao butter, rice bran oil, soybean oil, tsubaki oil, rape seed oil, palm oil, palm kernel oil, caster oil, cotton seed oil, japan wax, coconut oil, peanut oil, sunflower oil and the like, animal oils such as tallow, butterfat, mutton tallow, neats foot oil, whale oil, cod liver oil, sardine oil, orange roughy oil, herring oil and the like, hydrogenated oils of such oils. Examples of useful natural waxes are spermaceti, insect wax, carnauba wax, candelilla wax, rice bran wax, shellac, beeswax, montan wax, wool wax, cotton wax and the like.

For the reaction of this invention, these fatty acid esters are usable singly, or at least two of them can be used in admixture.

The process of the invention can be practiced batchwise, semicontinuously or continuously. In any of these cases, the reaction can be conducted by bringing the component (1) and component (2) as substrates into contact with the above-mentioned enzyme or immobilized enzyme. While the reaction merely proceeds when the substrates are contacted with the enzyme, it is usually desirable to mix them together by stirring. Our research has revealed that the reaction readily proceeds in an aqueous medium system or water-containing organic solvent system (containing the two phases of water and an organic solvent) and that the synthesis ratio of the desired product is almost free of the influence of the reaction system.

The term "aqueous medium system" refers to a reaction system comprising the enzyme, substrates, and water or the combination of water and a hydrophilic substance for dissolving the enzyme. The term "water-containing organic solvent system" refers to a system comprising a water-containing organic solvent capable of dissolving at least one of the substrates, i.e., a system comprising the substrates, enzyme activated with water, or with the combination of water and a hydrophilic substance, and a water-containing organic solvent capable of dissolving at least one of the substrates. The term "water-containing organic solvent" means an organic solvent containing water to saturation or in a larger quantity. When the water content of this system exceeds the solubility of the organic solvent, the system comprises two phases, i.e., water and the organic solvent. In the case of this water-organic solvent two-phase system, the aqueous phase containing the enzyme (or the enzyme and the hydrophilic substance) can be separated from the organic solvent phase containing the substrates and the solvent by allowing the system to stand or subjecting the system to centrifuging, selective filtration or the like. These terms as hereinafter used have the same meaning as above.

The hydrophilic substance is a substance which is miscible with water. Desirable as such a substance is one which will not inactivate the enzyme to the greatest possible extent, such as glycerin. The organic solvent to be used for the water-containing organic solvent phase is desirably one which is not miscible with water and which will not inactivate the enzyme to the greatest possible extent. Examples of useful organic solvents are hydrocarbon solvents such as n-hexane, n-heptane, n-octane, isooctane, cyclohexane, n-decane, n-tridecane, n-tetradecane, n-hexadecane, polybutene, diisobutylene, fluid paraffin, squalane, squalene, pristane and the like. Similarly usable are mixtures of at least two of these hydrocarbons and solvents containing such hydrocarbons, such as "IP solvent 1016" (product of Idemitsu Petrochemical Co., Ltd., isoparaffin-type mixture comprising 63% of $C_8$ component and 30% of $C_9$ component), and "ISOPAR E" (product of Exxon Chemicals, isoparaffin-type mixture comprising 25-35% of $C_8$ component and 75-60% of $C_9$ component).

Generally in synthesizing glycerides with use of an enzyme, the water content of the reaction system is a very important factor. In order to shift the equilibrium of the reaction in the direction toward synthesis, it is essentially required to reduce the water content to the greatest possible extent except a minimum quantity of water required for the enzyme to exhibit its activity. According to the present invention, the synthesis reaction proceeds favorably rapidly even when the reaction system contains a large amount of water. The reaction proceeds smoothly also in the water-containing organic solvent system.

Especially when the two-phase system of water and organic solvent is used as the above-mentioned system, the resulting reaction mixture contains the enzyme as distributed through the aqueous phase or over the interface between the water and the organic solvent, and the desired ester and unreacted substrates as distributed through the organic solvent phase. Consequently, the enzyme can be easily separated from the desired ester and unreacted substrates. Further when the organic solvent is used, sterols and higher aliphatic alcohols in solid form can be subjected to the reaction as dissolved in the solvent. This serves to improve the properties of the reaction mixture to advantageously effect the contact between the enzyme and the substrates.

The reaction conditions need only to be such that the inactivation of the enzyme used is avoidable or minimized. Usually, an optimum pH and optimum temperature for the enzyme are used. This temperature is usually about 10° to about 60° C. When a thermostable enzyme such as thermostable lipase is used, a higher temperature is usable accordingly. The pH to be used is in accordance with the kind of enzyme used. When required, the pH is adjustable by adding to the reaction system a suitable acid or alkali, such as hydrochloric acid, sulfuric acid, sodium hydroxide or potassium hydroxide, or a suitable buffer such as phosphate buffer. The reaction system may further contain an enzyme activator such as casein, albumin, calcium ion, bile acid or salt thereof, and a surfactant, which does not inhibit the enzyme activity, for assuring the contact between the substrates and the enzyme more effectively, such as "Tween 80" (product of Kao Atlaes Co., Ltd.) and "Triton X-100" (product of Rohm & Haas).

The reaction system contains the enzyme and the substrates in a ratio which is not limited specifically but which can be suitably determined according to the kind of these substances, reaction conditions and method of practicing the present process, i.e., batchwise, continuous or semicontinuous (repetition method). Usually, for one run of reaction, about 1 to about one million units, preferably about 500 units to about 100,000 units, of lipase, or about 1 unit to about one million units, preferably about 5 units to about 100,000 units, most preferably about 50 units to about 50,000 units, of cholesterol esterase can be used per gram of the alcoholic starting material (component (1)). The ratio between the component (1) and the component (2) can be determined suitably without any specific limitation, and either one can be used in an excessive amount. Usually, one substrate is used in an amount of about 0.1 to about 20 moles per mole of the other substrate.

For the enzyme to exhibit synthesis activity, at least about 10 mg of water is required per gram of the enzyme (completely dry weight). The water is contained usually in the enzyme preparation, immobilizing carrier or substrates. Generally when an aqueous medium reaction system is to be used, the water content of the system, which is required for the activity of the enzyme, also relates to the state of contact between the enzyme and the substrates. To assure satisfactory contact and achieve a sufficient reaction velocity, water is used preferably in about 7 to about 10,000 times, more preferably about 15 to about 700 times, the amount of the enzyme by weight. In the case of a water-containing organic solvent system, the water saturating the organic solvent provides a sufficient amount of water required for the exhibition of the activity of the enzyme. When a fatty acid ester is used as one of the substrates, it is thought that the hydrolysis of the ester precedes the synthesis reaction, and the water in the system is partly consumed for the hydrolysis reaction. Accordingly, if the amount of water is limited to a quantity saturating the organic solvent, a reduced synthesis reaction velocity could result. It is therefore usually desirable that the reaction system have a water content in excess of the solubility of the organic solvent to serve as a water-organic solvent two-phase system. Alternatively it is desirable to use an immobilized enzyme retaining a sufficient amount of water in its immobilizing carrier. This assures a high synthesis reaction velocity and a high yield.

When the water-organic solvent two-phase system is used which has a water content in excess of the solubility of the organic solvent, the enzyme is present locally in the aqueous phase and at the water-solvent interface, so that the enzyme can be separated from the substrates for reuse, by separating the aqueous phase from the organic solvent phase, hence advantageous.

The water-to-solvent ratio of the water-containing organic solvent system, especially the amount of water present in the system, influences the reaction velocity to some extent. It is therefore desirable to determine the amount of water according to the kind of substrates to be used, kind of enzyme and solvent, method of mixing these substances, shape and size of the reactor, overall volume of reaction system and other reaction conditions. For example, when a sterol is to be reacted with a fatty acid in a water-containing organic solvent system wherein isooctane is used, it is preferable to use isooctane in about 0.001 to about 100 times, more preferably about 0.01 to about 10 times, the amount of water by weight. In this case, the water-containing organic solvent is used preferably in about 5 to about 500 times the amount of the sterol by weight.

Although the present process can be practiced batchwise, it is desirable to practice the process cotinuously or semicontinuously, since the enzyme which is relatively expensive can then be used at least twice repeatedly. The methods wherein the enzyme is used at least twice are divided generally into two types: semicontinuous methods (repetition of batchwise method) and continuous methods depending on whether the enzyme or immobilized enzyme is separated from the reaction mixture after the first run of contact reaction. The methods of each type are further divided as follows depending on whether the immobilized enzyme or native enzyme is used.

When the process of the invention is practiced with use of the native enzyme either continuously or semicontinuously, phase separation, suitable filtration means or centrifugation is resorted to.

When phase separation is utilized for practicing the present process semicontinuously, the procedure comprises adding water and/or an organic solvent to the reaction mixture resulting from the first reaction to convert the mixture to a system of two phases, i.e., an aqueous phase and a hydrophobic substrate phase (or allowing the mixture to stand as it is in the case of water-organic solvent two-phase system), separating the aqueous phase from the hydrophobic substrate phase by standing or centrifugation to separate the enzyme present in the aqueous phase and at the water-solvent interface from the organic phase containing the desired ester and unreacted substrates, and repeatedly using the separated enzyme. The addition of the organic solvent to the aqueous medium system for the phase separation is effective for promoting the separation by breaking emulsification of the reaction mixture. The separated organic phase is subjected to liquid-liquid extraction utilizing a distribution coefficient difference, for example, to extraction with an aqueous solution of lower alcohol such as methanol, whereby the unreacted substrate such as highly polar sterol or higher aliphatic branched alcohol material is extracted into the aqueous alcohol solution and can thereby be separated from the desired ester easily and efficiently.

When the reaction system is a water-containing organic solvent system but is not a water-organic solvent two-phase system, the enzyme, which is insoluble in hydrophobic substrates and organic solvents, is suspended in the reaction system in the form of particles. Accordingly, when filtration is to be resorted to in this case, the enzyme can be separated off by a suitable filtration method such as microfiltration or ultrafiltration. Microfiltration can be conducted using usual filter paper and a filter aid in combination. In this case, the enzyme is captured by the agent as adsorbed thereto and is usable in this state. A membrane filter or the like is also usable for microfiltration. Preferably the filter is about 0.02 to about 10 $\mu$m in pore size. Examples of useful materials for such filters are inorganic materials having high resistance to chemicals, such as glass and metal, and organic materials such as regenerated cellulose, Teflon, polypropylene, polyamide, polyimide and like synthetic resins.

When the reaction system is an aqueous medium system, ultrafiltration is resorted to for separating off the enzyme for reuse. Ultrafiltration can be carried out using various ultrafilters which are usually commercially available and which are made of chemically resistant materials such as polyamide, polyimide, high polymer electrolyte composite material, etc.

Further in the case of a water-organic solvent two-phase system, the aqueous phase can be separated from the oily or organic solvent phase by filtration utilizing the selective permeability of hydrophobic porous separation membranes. More specifically stated, hydrophobic substrates and organic solvents can penetrate through micropores of the hydrophobic separation membrane, whereas water and enzymes, which have great surface tension, are unable to wet the surface of the membrane and to pass through the micropores. This makes it possible to separate the enzyme from the substrates and reaction product by filtration. The hydrophobic separation membranes to be used for this method are those greater than the hydrophobic substances but smaller than water in critical surface tension, for example, those about 30 to about 55 dynes/cm in critical surface tension. The pores of these membranes need not always be smaller than the enzyme particles but can be up to about 10 $\mu$m in pore size. Examples of useful membranes are commercial microfiltration membrane filters which are made of hydrophobic Teflon and polypropylene.

When the above-mentioned phase separation is resorted to for practicing the process of the invention continuously, the continuous method is conducted using, for example, an native enzyme in the form of an aqueous solution or as dissolved in an aqueous solution of a hydrophilic substance usable for the aforementioned aqueous medium system (when the term aqueous solution is hereinafter used for the enzyme, the term is to be interpreted as including the aqueous solution of hydrophilic substance), and employing a suitable reactor which has a reaction unit for contacting and reacting the aqueous enzyme solution with the substrates or an organic solvent solution thereof and a separation unit for effecting phase separation. Thus, the reaction and phase separation are conducted continuously to repeatedly use the aqueous enzyme solution while continuously obtaining the desired product from the separated organic phase. An oily phase or organic solvent phase containing the substrates is continuously fed to the reaction unit.

The reactor suitable for practicing the continuous method can be any of various known ones (Kagaku Kogaku (Chemical Engineering) III, published by Tokyo Kagaku Dohjin, 1964). Typical examples of suitable reactors are the mixer-settler type and the spray tower type.

The reactor of the mixer-settler type comprises the combination of a mixer and a settler for separating a mixture by gravity difference. To use the reactor, the substrates or an organic solvent solution thereof is continuously fed to the mixer which is filled with the aqueous enzyme solution, while the aqueous enzyme solution is contacted and reacted with the substrates or the solution thereof in the mixer with stirring at the same time. The reaction mixture is sent to the settler. While staying in the settler, the reaction mixture is separated into an aqueous phase and a substrate phase or organic solvent phase containing the desired product (reaction mixture). While returning the enzyme-containing aqueous phase to the mixer, the reaction mixture (upper layer) is drawn off from the settler. Thus, the product is continuously obtained.

According to the method employing a spray tower, the aqueous enzyme solution, or the substrates or the solution thereof in a water-immiscible organic solvent is caused to ascend or descend the interior of the tower as a dispersed phase for reaction. It is especially desirable to use the substrate phase as the dispersed phase since it is then unnecessary to circulate the enzyme phase. This desirable method is practiced by placing the aqueous enzyme solution into the tower as a continuous phase, continuously supplying the substrate phase to the tower through a nozzle at a lower portion of the tower to cause the dispersed phase to rise through the liquid column of enzyme solution to effect contact therebetween and separate the phase containing a reaction product from the continuous phase at the top of the tower, and continuously or successively drawing off the separate the phase containing a reaction product from the continuous phase at the top of the tower, and continuously or successively drawing off the separated phase from the top. Usually, the continuous phase of aqueous enzyme solution charged into the tower need not be replaced until the activity of the enzyme decreases, while the enzyme solution can be replenished with fresh portions from time to time when the activity reduces. Since the reaction takes place at the interface between the ascending drops of substrate phase and the aqueous enzyme solution within the tower, this method assures effective contact during the initial stage of formation of drops and when the drops coalesce as generally the case with liquid-liquid extraction. In this respect, it is desirable to repeat formation and extinction of drops many times. Accordingly, circulation of the substrate phase is effective for improving the synthesis ratio of the desired ester. Further the reaction velocity can be improved by decreasing the size of drops, increasing the concentration of enzyme or decreasing the speed of rise of the drops to extend the contact time.

The spray tower method can be practiced more efficiently, for example, by using a tower having perforated plates arranged in stages at intermediate portions of the tower. The light substrate dispersed phase passes through the perforations of the plate in the first stage in the form of drops, which flow upward through the continuous phase of heavy aqueous enzyme solution while contacting and reacting therewith. The drops aggregate to form a liquid phase beneath the perforated plate in the second stage, and the liquid phase is then made into drops again upon passing through the second perforated plate upward. This procedure is repeated. Accordingly formation and extinction of drops are repeated a number of times within the tower having the perforated plates to achieve an improved efficiency.

Similarly advantageously usable are a tower having a multiplicity of baffle plates in the flow channel within the tower to prolong the period of contact between the two phases, a tower packed with a suitable material in place of the perforated or baffle plates, a tower internally equipped with a rotary hollow cylindrical or disk-like stirrer and adapted to effect mechanical agitation, a tower (Scheibel tower) having a packed material and stirring means alternately arranged in layers, a pulsating extractor for effecting agitation by pulsation instead of mechanical agitation, Podbielniak extractor, Luwesta extractor and like centrifugal extractors utilizing a centrifugal force afforded by high-speed rotation. These devices can be used in combination.

The process of the present invention further includes a method wherein the hydrophilic aqueous enzyme solution is placed on one side of a porous reaction membrane, and the hydrophobic substrates or the solution thereof in a water-containing organic solvent is placed on the other side of the membrane to contact the enzyme solution with the substrate phase through the micropores of the membrane and to react the substrates. By this method, the desired ester can be prepared, and the enzyme is repeatedly usable without mixing the enzyme solution with the substrates.

In this case, the enzyme is separated from the substrates by the membrane without mixing and is brought into contact with the substrates through the micopores of the membrane, so that the reaction mixture can be withdrawn from the system continuously while continuously supplying the substrates to the one side of the membrane. This method therefore does not permit emulsification of the reaction mixture, ingress of the enzyme protein into the substrate phase or reduction of enzymatic activity due to the substrates, further rendering the reaction free of adverse effect due to the enzyme stabilizer or the like added to the aqueous phase. Further because the reaction can be carried out at room temperature in a hermetic state, the reaction does not involve side reactions such as autoxidation of the substrates, isomerization or shift of double bond even when the substrates have low stability to oxidation.

The material for the porous reaction membrane to be used for the above method is not limited specifically. Examples of useful materials are inorganic materials such as glass, ceramics, stainless steel netting and porous stainless steel, synthetic resins such as Teflon, polypropylene, polyethylene and like polyolefins, cellulose derivatives such as regenerated cellulose, nitrocellulose and acetylcellulose, and organic materials such as nylon 66 and like polyamides, polycarbonate and the like. It is suitable that the membrane have a pore size usually of about 0.05 μm to about 10 μm. Typical of such membranes are commercial membrane filters for microfiltration. Well known as such membrane filters are hydrophilic filters made of acetylcellulose, nitrocellulose, regenerated cellulose and the like, and hydrophobic filters made of Teflon, polypropylene and the like. Any of these filters is usable for the present invention. As other preferred properties, it is desirable that the reaction membrane be about 10 to about 100 μm, more desirably about 20 to about 50 μm, in thickness and 20 to 80%, more desirably about 40 to about 60%, in porosity. The membrane is not specifically limited in shape and may be planar as usual. However, it is preferably hollow cylindrical, spiral, tubular or in the form of a hollow fiber. When having such a shape, the membrane permits contact between the enzyme and the substrates over a larger area than when it is planar to shorten the reaction time and achieve an improved synthesis ratio.

When the reaction membrane is used for the present process, the aqueous enzyme solution comes into contact with the hydrophobic substrates through the micropores of the membrane for reaction. If the membrane is hydrophobic, the hydrophobic substrates penetrate into the enzyme solution through the micropores of the membrane. It is therefore desirable to apply pressure to the enzyme solution to avoid this objection. This pressure varies depending on the kind of membrane material. The upper limit for the pressure is usually a value permitting the water to penetrate through the micropores of the membrane against the repellency afforded by the surface tension of water thereon, i.e., water initiation value. Generally, the pressure is preferably in the range of from about 0.001 to about 20 kg/cm². When the membrane is hydrophilic, it is desirable to apply pressure of about 0.001 to about 20 kg/cm² to the substrate side in order to prevent the aqueous enzyme solution from penetrating into the substrate side through the membrane micropores. The aqueous enzyme solution supplied to one side of the membrane need not be replaced or replenished usually until the activity thereof decreases, nor is it required to stir or circulate the solution. The substrate phase supplied to the other side contacts with the enzyme for reaction through the membrane micropores. The synthesis ratio increases with an increase in the contact time. The synthesis ratio can be improved with a shortened contact time by increasing the area of contact between the enzyme and the substrates.

The present invention further includes use of an immobilized lipase or cholesterol esterase for practicing the process. The immobilized enzyme can be prepared using a suitable carrier by various known methods, typical of which are, for example, entrapping method, inorganic carrier covalent bond method, organic carrier covalent bond method, adsorption method, etc. These methods will be described in detail below.

The entrapping method can be practiced using various known carriers. Because the substrates to be used for the present reaction are hydrophobic, preferred carriers are those permitting the substrates to penetrate into gels easily and having a great distribution coefficient for the hydrophobic substances. Examples of such carriers are hydrophobic photo-crosslinkable resin prepolymers such as ENTP represented by the formula (1) below (see European J. Appli. Microbiol. Biotechnol., 5, 325(1979) and Unexamined Japanese Patent Publication SHO 57-118792), and urethane prepolymer PU represented by the formula (2) below (see Biotechnol. Bioeng., 20, 1,465–1,469(1978) and Eur. J. Appln. Microbiol. Biotechnol., 8, 143–155(1979)).

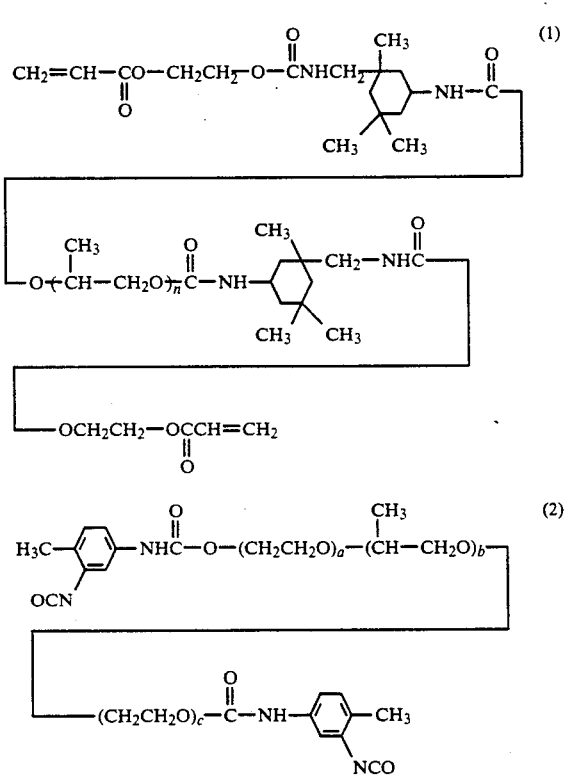

The hydrophobicity of these resins can be altered as desired by varying the propylene oxide content of the molecule in the case of ENTP resin, or by varying the EO/PO content for PU resin.

The entrapping method can be practiced with use of ENTP or like hydrophobic photo-crosslinkable resin prepolymer, for example, by adding a photosensitizer to ENTP-4000 having a chain length of 40 nm, warming the mixture at about 60° C. to obtain a melt, cooling the molten mixture to 4° C., admixing with the mixture the enzyme in a powder form or as adsorbed by a porous inorganic carrier such as celite or silica (a suitable surfactant or the like can also be added in this step), spreading the resulting mixture over a transparent glass or polyester plate, covering the spread mixture with a plastic cover to eliminate air, illuminating the mixture with chemical lamps (wavelength range, 300–400 nm; maximum intensity at 360 nm) for several minutes to effect gelation, and cutting the resulting gel film of immobilized enzyme into small pieces, whereby the desired immobilized enzyme is obtained.

The entrapping method can be practiced with use of PU resins, e.g., highly hydrophobic PU-3 (2,529 in average molecular weight, 4.2% in NCO content, 57% in ethylene oxide content, see the above literature), by heating the resin to about 50° C. to fluidize the resin, then cooling the resin to 30° C., adding an aqueous enzyme solution to the resin while it is still flowable, kneading the mixture for several minutes until gelation starts, maintaining the mixture at 4° C. for about 60 minutes to complete gelation, cutting the gel block, thus formed to a suitable size, and washing the product with water to remove the unreacted NCO groups, whereby the desired immobilized enzyme preparation is obtained. If the reaction temperature exceeds 30° C., the enzyme could be partially inactivated, so that care should be taken to avoid the objection.

Inorganic or organic carriers useful for the covalent bond method are preferably microporous carriers having a hydrophobic porous surface. Usually, the pores have an average radius of about 10 Å to about 1,000 Å. Insofar as the pores give the carrier an increased enzyme bonding area per particle of the carrier, the pores may have, for example, an elongated shape such that the radius of the pores can not be determined. Examples of preferred carriers are inorganic carriers including porous glass, porous ceramics, celite, porous metallic particles such as titanium oxide, alumina, porous silica gel, molecular sieve, active carbon, clay, kaolinite, bentonite, hydroxyapatite, calcium phosphate gel and alkylamine derivatives of such materials, and organic carriers including microporous adsorbing resins such as one made basically of styrene or alkylamine polymer, chelate resin, ion exchange resin such a "DOWEX MWA-1" (weaky basic anion exchange resin manufactured by the Dow Chemical Co., having a tertiary amine as the exchange group, composed basically of polystyrene chains crosslinked with divinylbenzene, 150 Å in average pore radius and 20-50 mesh in particle size), and hydrophilic cellulose resin such as one prepared by masking the hydrophilic group of a cellulosic carrier, e.g., "Cellulofine GC700-m" (product of Chisso Corporation, 45-105 μm in particle size).

The covalent bond method can be practiced for immobilizing the enzyme using such inorganic carriers, for example, by preparing an alkylamine derivative of the inorganic carrier, giving enhanced hydrophobic properties to the porous surface of the carrier and immobilizing the enzyme by the glutaraldehyde method or carbodiimide method [see H. H. Weetall, Methods in Enzymology, 44, 134-148(1976)].

When a hydrophobic porous resin is used as the organic carrier for the covalent bond method, the method can be practiced by causing the resin to adsorb the enzyme, followed by the glutaraldehyde method [see Rev. Ferment. Ind. Aliment, 11, 237(1956)]. Stated more specifically, the covalent bond method can be practiced, for example, with use of DOWEX MWA-1, by washing the resin (1 g) with distilled water and 1/15 M of McIlvaine buffer (pH 5.0), adding 0.2 ml (1,500 U) of enzyme solution, shaking the mixture at 8° C. overnight for adsorption, adding 1 ml of McIlvaine buffer and 80 μl of 25% glutaraldehyde solution to the mixture, shaking the resulting mixture at 8° C. for 10 minutes to bond the enzyme to the resin, adding 0.2 ml of 20% sodium bisulfite, shaking the mixture at 80° C. for 10 minutes to remove an excess of glutaraldehyde, and washing the resulting mixture.

When a hydrophilic resin, such as Cellulofine GC700-m, is used as the organic carrier, the method can be practiced by epoxidizing hydrophilic hydroxyl groups present on the surface of the resin, aminating the epoxidized resin with ethylenediamine, treating the resin with glutaraldehye to obtain aldehydized resin and reacting the resin with the enzyme in phosphate buffer.

Carriers useful for the adsorption method are organic carriers prepared by modifying hydrophilic polysaccharides such as agarose gel with an alkyl, phenyl, trityl or like hydrophobic group to provide a hydrophobic porous surface, e.g., "Octyl-Sepharose CL-4B", "Phenyl-Sepharose CL-4B" (both products of Pharmacia Fine Chemicals) and trityl agarose gel, and inorganic carriers including the same as those exemplified above in the covalent bond method. The hydrophobicity of the above-mentioned organic carriers can be increased by giving an increased amount of nonpolar hydrophobic alkyl groups, or by modifying hydroxyl and like hydrophilic groups with an alkyl group or the like.

With use of such organic carriers, the adsorption method can be practiced, for example, by thoroughly washing the carrier with phosphate buffer or the like and thereafter shaking the carrier and the aqueous enzyme solution together to cause the carrier to adsorb the enzyme. This method gives a high immobilizing yield as compared with the covalent bond method. Moreover, the carrier, which comprises a hydrophilic gel having hydrophobic ligands attached thereto, retains and affords a sufficient amount of water needed for the enzyme to exhibit its activity. The carrier is further given enhanced affinity for the hydrophobic substrate by the modification of hydrophobic group. Accordingly, the immobilized enzyme prepared by the method is especially suited to the present process.

When an inorganic carrier is used for the adsorption method, the method can be practiced merely by shaking the carrier and the aqueous enzyme solution together. This method is most convenient and inexpensive, less likely to lower the activity of the enzyme when immobilizing, and physically and chemically stable.

When the process of the present invention is to be practiced batchwise or semicontinuously using the enzyme immobilized by one of the foregoing methods, the immobilized enzyme and the substrates are placed, for example, into a suitable reactor to react the substrates in contact with the enzyme in an aqueous medium system and/or water-containing organic solvent system. In the case of semicontinuous method, the immobilized enzyme is separated from the resulting reaction mixture in usual manner, for example, by filtration or centrifugation and is used repeatedly for the subsequent reaction cycle. The reaction can be carried out under suitable conditions that will not destroy the immobilized enzyme, e.g. with shaking or passing the substrate solution through the enzyme for contact. The desired ester can be collected from the reaction mixture separated from the immobilized enzyme, in the same manner as in the foregoing methods employing phase separation technique.

The present process can be practiced continuously with use of the immobilized enzyme, for example, by packing the enzyme in a suitable column, continuously passing the substrates or a water-containing organic solvent solution thereof though the column for contact and reaction, continuously collecting the reaction mixture and separating the desired ester from the reaction mixture. Irrespective of whether the semicontinuous method or continuous method is resorted to, the immobilized enzyme can be recovered easily. This eliminates the need to remove the enzyme protein in the step of purifying the desired ester and assures reuse of the recovered enzyme, hence advantageous. Additionally, the continuous method involves a reduced likelihood of permitting exposure of the substrates to air during reaction and therefore has the advantage that unsaturated fatty acids or the like, if used, will not be oxidized with air.

The desired ester obtained by the present process is separated from the reaction mixture by a usual method and, when required, is purified. In the case of batchwise method, the desired product can be separated from the reaction mixture, for example, by subjecting the mixture to extraction using a suitable solvent such as ether, removing the unreacted fatty acid material with an alkali, dehydrating and drying the solvent layer, and removing the solvent from the layer. The desired product can be purified, for example, by column chromatography.

The desired ester thus obtained is usable for a wide variety of applications for which esters of the same type are usually used.

EXAMPLES

The examples to be given below are further illustrative of the present invention.

It should be understood that the amounts of enzymes indicated in the examples are the international units determined by the following methods.

Lipase Activity

To 75 ml of polyvinyl alcohol solution [18 g of Poval #117 (Kurashiki Rayon Co., Ltd.) and 2 g of Poval #205 (the same manufacturer as above) are suspended in 800 ml of water, stirred at 75°–80° C. to complete dissolution, cooled and water is added to make a total of 1,000 ml] is added 22.9 g of olive oil and the mixture is emulsified with a homogenizer. To 5 ml of the emulsion thus obtained is added 4 ml of 0.1 M phosphate buffer, followed by addition of 1 ml of an enzyme solution. The mixture is stirred with a magnetic stirrer at 500 rpm at 37° C. for 20 minutes. After 40 ml of ethyl alcohol is added, the free fatty acid is titrated with 0.05 M potassium hydroxide. The amount of the enzyme which liberates 1 $\mu$mole equivalent of fatty acid in 1 minute under the above conditions is taken as one international unit (U).

Cholesterol Esterase Activity

One unit (1 U) of cholesterol esterase is the activity which liberates 1 $\mu$mole of cholesterol from calf serum in 1 minute at 37° C. It is determined by oxidizing the free cholesterol with cholesterol oxidase using the following reagent and enzyme solutions and estimating the product hydrogen peroxide colorimetrically using peroxidase.

| Reactant composition | |
|---|---|
| 0.2 M phosphate buffer (pH 6.5) | 0.6 ml |
| Peroxidase (Sigma Chemical, Type II No. P-8250) | 0.3 ml |
| 4-Aminantipyrin (0.35% aqueous solution) | 0.3 ml |
| Phenol (0.2 w/w % aqueous solution) | 0.3 ml |
| Cholesterol oxidase [prepared by diluting Product No. T-04 (Toyo Jozo Co.,) with 0.1 M phosphate buffer (pH 7.0, containing 0.05 w/v % Triton X-100) to 10 U/ml] | 0.6 ml |
| Calf serum (Grand Island Biological, U.S.A.) | 0.3 ml |
| Distilled water | 0.3 ml |

The sample enzyme solution is prepared by dissolving the enzyme in 10 mM phosphate buffer (pH 0 7.5, containing 0.1% of albumin) to make a concentration of about 1 U/ml. A 3-ml portion of the above reactant composition is placed in a cell for colorimetry and incubated at 37° C. for 10 minutes, then 0.05 ml of the sample enzyme solution is added, mixing is effected by gently turning the cell upside down, and the absorbance is measured at 493 nm at timed intervals to thereby determine the rate of increase in absorbance ($\Delta$As/min). Using the buffer for dilution in place of the sample enzyme solution, the same procedure is performed and the rate of increase ($\Delta$Ab/min) is determined. If the difference between the above rates of increase in absorbance ($\Delta$A/min = $\Delta$As − $\Delta$Ab) is below 0.05, the concentration of the sample enzyme solution is increased and the procedure is repeated until said difference amounts to 0.05 or more. The enzyme activity is calculated as follows:

Enzyme activity (U/mg) =

$$\frac{\Delta A/min}{12.0 \times 0.5} \times \frac{3.05}{0.05} \times \frac{1}{\text{enzyme concentration (mg/ml)}}$$

The synthesis ratio of the desired ester is determined in the following manner. Thus, in Examples 1–14, the reaction mixture is acidified and extracted four times with diethyl ether, the extract is washed with water and dehydrated and dried, then the diethyl ether is distilled off and, to the whole lipid thus obtained, a known quantity of an internal standard (n-dotriacontane) is added to give a sample for quantitative determination. This sample is charged onto a Chromarod (quartz rod with silica gel fused thereto; product of Iatron; Chromarod S II), developed and submitted to an Iatroscan TH-10 (Iatron's FID—hydrogen flame ionization detector). The thus-determined quantity of the ester synthesized is divided by the theoretical quantity of the ester as calculated based on the quantity of the charge to give the synthesis ratio in percentage. In Examples 15–65, the reaction mixture is converted to a water-organic solvent two-phase system, the organic solvent phase is separated and, after adjustment to an appropriate concentration, charged onto the above-mentioned Chromarod in an amount corresponding to 10–30 $\mu$g of lipid, and developed under appropriate conditions causing separation of the desired ester from the unreacted substrates (e.g. hexane/ether/formic acid = 56/14/0.3). If necessary, a silver nitrate-impregnated Chromarod, for instance, is used for the separation of components. After development, the Chromarod is dried for several minutes and submitted, in the developing solvent-free state, to Iatroscan TH-10 to thereby determine the peak area for the lipid component in the reaction mixture. The synthesis ratio of the desired ester is calculated based on the above area using the equation given in the corresponding example.

In each of the examples, unless otherwise specified, the reaction was carried out in a constant-temperature room maintained at 37° C., stirring of the reaction mixture was effected with a reciprocating shaker (20 mm × 300 cpm; Iwashiya Bio-Science Co., Ltd., model RMR-S-20) and the organic solvents were used as saturated with water.

In Examples 1–8, the enzyme used was *Candida cylindracea*-derived lipase ("Lipase MY"; product of Meito Sangyo Co., Ltd.). The enzymes used in other examples are given in the respective examples.

EXAMPLE 1

In this example, the correlation between the rate of ester synthesis (synthesis ratio) and the quantitative ratio between the substrates was investigated by conducting the reaction in several runs in which 100 mg of cholesterol and a varying amount of oleic acid were used as the sterol and fatty acid, respectively, and brought into contact with each other in the presence of 0.5 ml (500 U) of an aqueous solution of lipase with stirring for 18 hours. The results thus obtained are shown below in Table 1.

TABLE 1

| Run No. | Oleic acid amount (mg) | Synthesis ratio (%) |
|---|---|---|
| 1 | 70 | 58.5 |
| 2 | 100 | 77.9 |
| 3 | 150 | 83.0 |
| 4 | 220 | 87.7 |
| 5 | 290 | 88.6 |
| 6 | 370 | 89.7 |
| 7 | 440 | 91.8 |
| 8 | 660 | 92.0 |

The data in Table 1 indicate that when oleic acid is about 1-6 times the amount by weight of cholesterol, the desired ester, cholesteryl oleate, can be synthesized in a ratio of not less than about 80%. It is further indicated that when oleic acid is used in an amount of 2-6 weight parts (3-9 moles) per weight part (mole) of cholesterol, the esterification is rapid and the synthesis ratio of the desired ester is maximum.

EXAMPLE 2

In this example, what influences the water content in the reaction system has on the synthesis ratio of the desired ester was examined. Thus, the reaction was carried out using 100 mg of cholesterol, 220 mg of oleic acid and 0.5 ml (500 U) of an aqueous lipase solution under the same conditions as used in Example 1 except that 0.5 ml, 1.0 ml, 2.0 ml, 4.0 ml, 6.0 ml or 10.0 ml of water was added to the system. The synthesis ratio attained in the respective runs (after 18 hours) are shown below in Table 2.

TABLE 2

| Run No. | Amount of water (ml) | Synthesis ratio (%) |
|---|---|---|
| 1 | 0 | 87.5 |
| 2 | 0.5 | 97.6 |
| 3 | 1.0 | 97.4 |
| 4 | 2.0 | 98.2 |
| 5 | 4.0 | 97.4 |
| 6 | 6.0 | 96.9 |
| 7 | 10.0 | 92.7 |

The data in Table 2 indicate that water should preferably be used in an amount of about 1-3 ml (about 10-30 weight parts per weight part of cholesterol).

EXAMPLE 3

In this example, the reaction was conducted in water-containing organic solvent systems. Thus, the reaction was carried out using 100 mg of cholesterol, mg of oleic acid, 0.5 ml (500 U) of an aqueous solution of lipase and a varying amount of isooctane, n-octane or n-hexane, each saturated with water, with stirring for 18 hours. The synthesis ratio of the ester as attained in this manner are shown below in Table 3.

TABLE 3

| Run No. | Solvent (ml) | Synthesis ratio (%) |
|---|---|---|
| 1 | Water (without organic solvent) | 87.5 |
| 2 | Isooctane (1) | 96.2 |
| 3 | Isooctane (2) | 96.7 |
| 4 | Isooctane (4) | 91.4 |
| 5 | Isooctane (6) | 83.4 |
| 6 | Isooctane (8) | 78.8 |
| 7 | Isooctane (10) | 67.6 |
| 8 | n-Octane (1) | 83.5 |
| 9 | n-Octane (2) | 78.1 |
| 10 | n-Octane (4) | 29.8 |
| 11 | n-Octane (6) | 13.9 |
| 12 | n-Octane (8) | 8.5 |
| 13 | n-Octane (10) | 7.7 |
| 14 | n-Hexane (1) | 76.4 |
| 15 | n-Hexane (2) | 68.8 |
| 16 | n-Hexane (4) | 29.6 |
| 17 | n-Hexane (6) | 11.0 |
| 18 | n-Hexane (8) | 9.5 |
| 19 | n-Hexane (10) | 6.6 |

The data in Table 3 indicate that the isooctane-involving systems are least in enzyme inactivation among the above systems. Isooctane, when added in an amount of 0.5-3 ml, markedly increased the synthesis ratio of the ester.

EXAMPLE 4

In this example, the reaction was carried out for 18 hours in the water-isooctane system by adding 2.0 ml of isooctane to a mixture of 100 mg of cholesterol, 220 mg of oleic acid and 0.5 ml (500 U) of an aqueous solution of lipase with a varying amount of water further added thereto. The thus-obtained synthesis ratio of the desired ester are shown below in Table 4.

TABLE 4

| Run No. | Amount of water (ml) | Synthesis ratio (%) |
|---|---|---|
| 1 | 0 (No addition) | 73.0 |
| 2 | 1 | 92.7 |
| 3 | 2 | 94.6 |
| 4 | 4 | 96.6 |
| 5 | 6 | 96.8 |
| 6 | 7 | 96.5 |
| 7 | 8 | 97.5 |
| 8 | 9 | 94.9 |
| 9 | 10 | 95.5 |

EXAMPLE 5

In this example, the reaction was carried out in the same manner and under the same conditions as in Example 4 except that the amount of water in the water-isooctane system was constantly 2.0 ml while the amount of isooctane was varied, and changes in the synthesis ratio of the desired ester were examined. The results obtained are shown below in Table 5.

TABLE 5

| Run No. | Amount of isooctane added (ml) | Synthesis ratio (%) |
|---|---|---|
| 1 | 0 (No addition) | 87.9 |
| 2 | 0.5 | 94.9 |
| 3 | 1.0 | 95.1 |
| 4 | 1.5 | 96.4 |
| 5 | 3.0 | 94.0 |
| 6 | 4.0 | 90.4 |
| 7 | 6.0 | 83.4 |
| 8 | 8.0 | 71.5 |

The data in Table 5 indicate that the combined use of 2 ml of water and 0.5–3.0 ml (5–30 times as large as the sterol amount) of isooctane markedly increases the synthesis ratio.

EXAMPLE 6

In this example, the fatty acid was a solid one and the reaction in water-organic solvent and the reaction in water were compared. The reaction was carried out using 100 mg of cholesterol, 220 mg of a solid fatty acid and 0.5 ml (500 U) of an aqueous lipase solution with stirring for 18 hours. For performing the reaction in water-organic solvent two-phase system, 2.0 ml of n-octane and 7.5 ml of water were further added to the reaction system whereas, for conducting the reaction in aqueous medium system, 2.0 ml of water was added to the reaction system. Palmitic acid and stearic acid were used each as the solid fatty acid. The results thus obtained are shown in Table 6. For comparison, the data obtained by using oleic acid, which is liquid at ordinary temperatures, are also given in Table 6.

TABLE 6

| | | Synthesis ratio (%) | |
|---|---|---|---|
| Run No. | Fatty acid | Water-organic solvent two-phase system | Aqueous medium system |
| 1 | Palmitic acid | 99.0 | 91.6 |
| 2 | Stearic acid | 98.5 | 51.6 |
| 3 | Oleic acid | 96.5 | 91.6 |

The data in Table 6 indicate that the use of water-organic solvent two-phase system significantly increases the synthesis ratio particularly when the acid is stearic acid.

EXAMPLE 7

In this example, 0.5 ml of a lipase solution having a varying concentration was added to the reaction system consisting of 100 mg of cholesterol, 220 mg of oleic acid, 2.0 ml of n-octane and 8.0 ml of water, and the correlationship between the enzyme concentration and the synthesis ratio of the ester was investigated. The reaction were conducted with stirring for 18 hours. The results thus obtained are shown in FIG. 1. In FIG. 1, the synthesis ratio of the ester (%) is on the ordinate and the enzyme amount (in international units, U) on the abscissa, the ratios of the ester as obtained by using the enzyme in varied amounts (given in U) being plotted against said enzyme amounts.

The data in FIG. 1 indicate that when about 5,000 U of the enzyme is used per 1,000 mg of cholesterol, the reaction can proceed rapidly and give the desired ester in high ratios.

EXAMPLE 8

In this example, lipase was used in that amount (about 100 U) found in Example 7 to give a synthesis ratio of about 30–40% at the end of 18 hours of reaction, and the enzymatic reaction period was further extended. In this way, the correlation between the reaction period and the ratio of the ester was studied. The results thus obtained are shown below in Table 7.

TABLE 7

| Run No. | Reaction period (hrs) | Synthesis ratio (%) |
|---|---|---|
| 1 | 16 | 45.6 |
| 2 | 24 | 57.7 |
| 3 | 40 | 65.8 |

TABLE 7-continued

| Run No. | Reaction period (hrs) | Synthesis ratio (%) |
|---|---|---|
| 4 | 48 | 70.0 |
| 5 | 64 | 74.4 |
| 6 | 72 | 74.9 |
| 7 | 96 | 78.0 |
| 8 | 120 | 79.8 |

The data in Table 7 indicate that even when the enzyme amount is 100 U, prolongation of the reaction period to 120 hours can result in production of the desired ester in a ratio of about 80%.

EXAMPLE 9

In this example, each combination of a sterol (in an amount of 100 mg), a fatty acid and an enzyme (in an amount of 0.5 ml solution) as given in Table 8 was used and the reaction was carried out in each reaction system given in Table 8 with stirring for 18 hours to give the corresponding desired ester. The data obtained in this manner are shown also in Table 8.

The symbols used in Table 8 and the subsequent tables for sterols, fatty acids, enzymes and organic solvents indicate the following:

| | Sterols |
|---|---|
| A-1 | Cholesterol |
| A-2 | β-Sitosterol |
| A-3 | Stigmasterol |
| A-4 | β-Cholestanol |
| A-5 | Ergosterol |
| A-6 | Isocholesterol |
| A-7 | Isotridecyl alcohol (product of Kuraray Co., Ltd.) |
| A-8 | NJCOL 200A (product of New Japan Chemical Co., Ltd.) |
| A-9 | Lanolin alcohol HH (product of Yoshikawa Oil and Fat Co., Ltd.) |
| A-10 | Fine oxocol 1800 (product of Nissan Chemical Industries, Ltd.) |
| | Fatty acids |
| B-1 | Oleic acid |
| B-2 | Palmitic acid |
| B-3 | Stearic acid |
| B-4 | Linoleic acid |
| B-5 | α-Hydroxypalmitic acid |
| B-6 | Lanolin fatty acids (product of Yoshikawa Oil and Fat Co., Ltd.) |
| B-7 | Propionic acid |
| B-8 | Capric acid |
| B-9 | Lignoceric acid |
| B-10 | Succinic acid |
| B-11 | Sebacic acid |
| B-12 | Isostearic acid (product of Emery Industries Inc.) |
| B-13 | FAIP (fatty acid of tall oil, main component are oleic acid and linoleic acid, product of Harima Chemicals, Inc.) |
| B-14 | Linolenic acid (Tokyo Kasei Kogyo Co., Ltd.) |
| | Enzymes |
| E-1 | Lipase MY (*Candida cylindracea*-derived lipase; 30 U/mg; product of Meito Sangyo) |
| E-2 | Lipase T-01 (*Chromobacterium viscosum*-derived lipase; 280 U/mg; product of Toyo Jozo) |
| E-3 | Lipase "Amano" A (*Aspergillus* species-derived lipase; 4 U/mg; product of Amano Pharmaceutical Co., Ltd.) |
| E-4 | Cholesterol esterase (*Pseudomonas* species-derived esterase; 100 U/mg; product of Funakoshi Yakuhin) |
| E-5 | Cholesterol esterase T-18 (105 U/mg; product of Toyo Jozo) |
| E-6 | Cholesterol esterase (*Candida cylindracea*-derived esterase; 20 U/mg protein; product of Seikagaku Kogyo) |
| E-7 | Lipase D-10 (*Rhizopus delemer*-derived lipase; |

|     |                                                                                                                                                   |
| --- | ------------------------------------------------------------------------------------------------------------------------------------------------- |
|     | 10 U/mg; product of Amano Seiyaku)                                                                                                                |
| E-8 | Lipase (*Rhizopus delemer*-derived lipase; 600 U/mg; product of Seikagaku Kogyo Co., Ltd.)                                                        |
| E-9 | Cholesterol esterase (pancreas-derived esterase; 11 U/mg; product of Oriental Yeast Co., Ltd.)                                                    |
|     | Organic solvents                                                                                                                              |
| S-1 | n-Octane                                                                                                                                          |
| S-2 | Isooctane                                                                                                                                         |
| S-3 | Cyclohexane                                                                                                                                       |
| S-4 | n-Hexadecane                                                                                                                                      |
| S-5 | "IP Solvent 1016" (isoparaffinic organic solvent mixture with $C_8$ content 63% and $C_9$ content 30%; product of Idemitsu Petrochemical)         |
| S-6 | "Isopar E" (isoparaffinic organic solvent mixture with $C_8$ content 25–35% and $C_9$ content 75–60%; product of Exxon Chemicals)                 |

TABLE 8

| Run No. | Enzyme (U) | Sterol | Fatty acid (moles based on sterol) | Water (ml) | Organic solvent (ml) | Synthesis ratio (%) |
| --- | --- | --- | --- | --- | --- | --- |
| 1  | E-1 (500)  | A-1 | B-1 (3)   | 8 | S-1 (2)   | 96.5 |
| 2  | E-1 (500)  | A-2 | B-1 (3)   | 8 | S-1 (2)   | 95.5 |
| 3  | E-1 (500)  | A-3 | B-1 (3)   | 8 | S-1 (2)   | 69.0 |
| 4  | E-1 (500)  | A-4 | B-1 (3)   | 8 | S-1 (2)   | 92.8 |
| 5  | E-1 (500)  | A-5 | B-1 (3)   | 8 | S-1 (2)   | 55.0 |
| 6  | E-1 (500)  | A-6 | B-1 (1.4) | 0 | S-2 (4.3) | 70.4 |
| 7  | E-1 (500)  | A-1 | B-1 (3)   | 8 | S-1 (2)   | 96.5 |
| 8  | E-1 (500)  | A-1 | B-2 (3)   | 8 | S-1 (2)   | 99.0 |
| 9  | E-1 (500)  | A-1 | B-3 (3)   | 8 | S-1 (2)   | 98.5 |
| 10 | E-1 (500)  | A-1 | B-4 (3)   | 8 | S-1 (2)   | 96.5 |
| 11 | E-1 (500)  | A-1 | B-5 (3)   | 8 | S-1 (2)   | 35.0 |
| 12 | E-2 (1000) | A-1 | B-6 (3)   | 2 | — (0)     | 55.0 |
| 13 | E-2 (1000) | A-1 | B-1 (3)   | 8 | S-2 (2)   | 85.3 |
| 14 | E-3 (1000) | A-1 | B-1 (3)   | 2 | S-2 (0.5) | 55.2 |
| 15 | E-4 (50)   | A-1 | B-1 (3)   | 8 | S-2 (2)   | 96.9 |
| 16 | E-5 (500)  | A-1 | B-1 (3)   | 8 | S-1 (2)   | 97.7 |
| 17 | E-5 (500)  | A-2 | B-1 (3)   | 8 | S-1 (2)   | 88.3 |
| 18 | E-6 (500)  | A-1 | B-1 (3)   | 8 | S-2 (2)   | 95.0 |
| 19 | E-3 (1000) | A-6 | B-1 (3)   | 8 | S-2 (2)   | 63.0 |
| 20 | E-1 (1000) | A-4 | B-3 (3)   | 8 | S-2 (2)   | 99.2 |

EXAMPLE 10

Esterification was conducted in a reaction system consisting of cholesterol (100 mg), a fatty acid given in Table 9 (in an amount of 3 moles per mole of sterol), an enzyme (1,000 U) given in Table 9 and a water-organic solvent two-phase system, isooctane/0.05 M phosphate buffer (pH 7)=3 ml/7 ml, for a period given in Table 9. The synthesis ratio for each desired ester as obtained in this manner are also shown in Table 9.

TABLE 9

| Run No. | Enzyme | Fatty acid | Reaction period (hrs) | Synthesis ratio (%) |
| --- | --- | --- | --- | --- |
| 1  | E-1 | B-7  | 48  | 65.4 |
| 2  | "   | B-8  | 18  | 94.3 |
| 3  | "   | B-6  | 48  | 85.5 |
| 4  | "   | B-5  | 72  | 72.7 |
| 5  | E-2 | B-6  | 120 | 74.1 |
| 6  | "   | B-8  | 120 | 89.4 |
| 7  | "   | B-9  | 72  | 77.0 |
| 8  | "   | B-11 | 120 | 42.4 |
| 9  | E-3 | B-10 | 120 | 27.0 |
| 10 | "   | B-8  | 120 | 55.8 |

EXAMPLE 11

The reaction was carried out using a reaction system consisting of 100 mg of cholesterol, 220 mg of oleic acid, 1,000 U of lipase MY and isooctane/0.05 M phosphate buffer (pH 7) =2 ml/8 ml, and changes of the synthesis ratio with time were followed. The results obtained are shown in Table 10.

TABLE 10

| Reaction period (hrs) | 0.5  | 1.0  | 1.5  | 2.0  | 3.0  | 4.0  |
| --- | --- | --- | --- | --- | --- | --- |
| Synthesis ratio (%)   | 83.7 | 94.0 | 97.5 | 98.0 | 98.4 | 98.5 |

EXAMPLE 12

In this example, the reaction was conducted using 100 mg of cholesterol, 220 mg of oleic acid, 500 U of lipase MY and organic solvent/0.05 M phosphate buffer (pH 7.0) =2 ml/8 ml for 6 hours, and changes of the cholesteryl oleate synthesis ratio depending on the kind of organic solvent were examined. The results obtained are shown in Table 11.

TABLE 11

| Run No. | Organic solvent | Synthesis ratio (%) |
| --- | --- | --- |
| 1 | S-2 | 97.0 |
| 2 | S-3 | 96.8 |
| 3 | S-4 | 96.7 |
| 4 | S-5 | 96.0 |
| 5 | S-6 | 96.0 |

EXAMPLE 13

A mixture of 10 g of cholesterol, 22 g of oleic acid, 50 ml of isooctane and 200 ml (50,000 U) of an aqueous solution of lipase MY was stirred at 200 rpm for 18 hours. Thereafter, ether was added and the mixture was washed with aqueous sodium bicarbonate to remove the aqueous layer. After several repetitions of this procedure, the ether layer was dried on anhydrous sodium sulfate. The ether was then distilled off to give cholesteryl oleate, which was a white semi-transparent crude product, in 96.3% purity and in a yield of 16.0 g (95.0%).

The thus-obtained crude product (6 g) was charged into a silica gel column (Wakogel C200, 160 g, product of Wako Pure Chemical Industries) and eluted with 2,000 ml of benzene to give 5.3 g of cholesteryl oleate. The infrared absorption spectrum (IR), melting point, color development on a thin-layer chromatography (TLC) plate and Rf value of this product were in complete agreement with those of reference standard cholesteryl oleate.

EXAMPLE 14

The reaction was effected for 45 hours by stirring a mixture of 1 g of cholesterol, 2.2 g of isostearic acid (product of Emery Industries), 0.333 g (10,000 U) of lipase MY, 30 ml of isooctane and 80 ml of 0.05 M phosphate buffer at 200 rpm. In the course of the reaction, the reaction mixture was sampled at timed intervals for determination of the synthesis ratio of the desired ester. The ratio was 28.5% in 3 hours, 85.9% in 23 hours and 91.0% in 45 hours.

The reaction was discontinued at 45 hours after starting the reaction, followed by extraction with aqueous methanol to remove the unreacted substrate. Distillation of the isooctane layer gave 1.53 g of unreacted isostearic acid and 1.54 g of the desired isostearic acid ester.

The thus-obtained cholesterol isostearic acid ester gave one single spot on a TLC plate and found to be 100% pure by Iatroscan analysis.

EXAMPLE 15

A mixture of 100 mg of cholesterol, 220 mg of oleic acid, 8 ml of isooctance, 8 ml of water and 500 U of lipase MY was stirred for 3 hours. Then, a sample was taken from the upper layer and analyzed for the synthesis ratio of cholesteryl oleate. Said ratio was calculated as follows:

$$\text{Synthesis ratio (\%)} = \frac{\text{(Desired ester peak area)}}{\text{(First component peak area + Desired ester peak area)}} \times 100 \quad (I)$$

The above term "first component" means that one of the two substrates charged as the reaction substrates which is smaller in the number of moles. For instance, if the fatty acid was charged in an amount of 3 moles per mole of the alcohol, the alcohol is the first component. According to the above equation, the ratio becomes 100% when the component charged in a smaller amount in terms of the number of moles has disappeared from the reaction mixture, independently of the remainder of the other component charged in excess. In the description that follows, the synthesis ratio data, unless otherwise specifically stated, are data calculated according to the above equation (I).

Thereafter, the reaction mixture was allowed to stand. The resulting upper isooctane layer was removed while leaving the interface portion in contact with water. To the remainder was added 5 ml of isooctane, the mixture was stirred and allowed to stand and the isooctane layer was removed, followed by the elimination of the unreacted substrates remaining in the interface portion and the reaction product by washing. After 5 repetitions of this procedure, 100 mg of cholesterol, 220 mg of oleic acid and 8 ml of isooctane were again added to the enzyme-containing aqueous layer, and the reaction was carried out for 3 hours.

The invention was practiced repeating the above procedure comprising treating the mixture for effecting the reaction, removing the upper, substrate- and reaction product-containing isooctane layer while leaving the lipase-containing aqueous layer and the interface layer, and adding the substrates and isooctane newly for the next reaction run.

Figure 2:
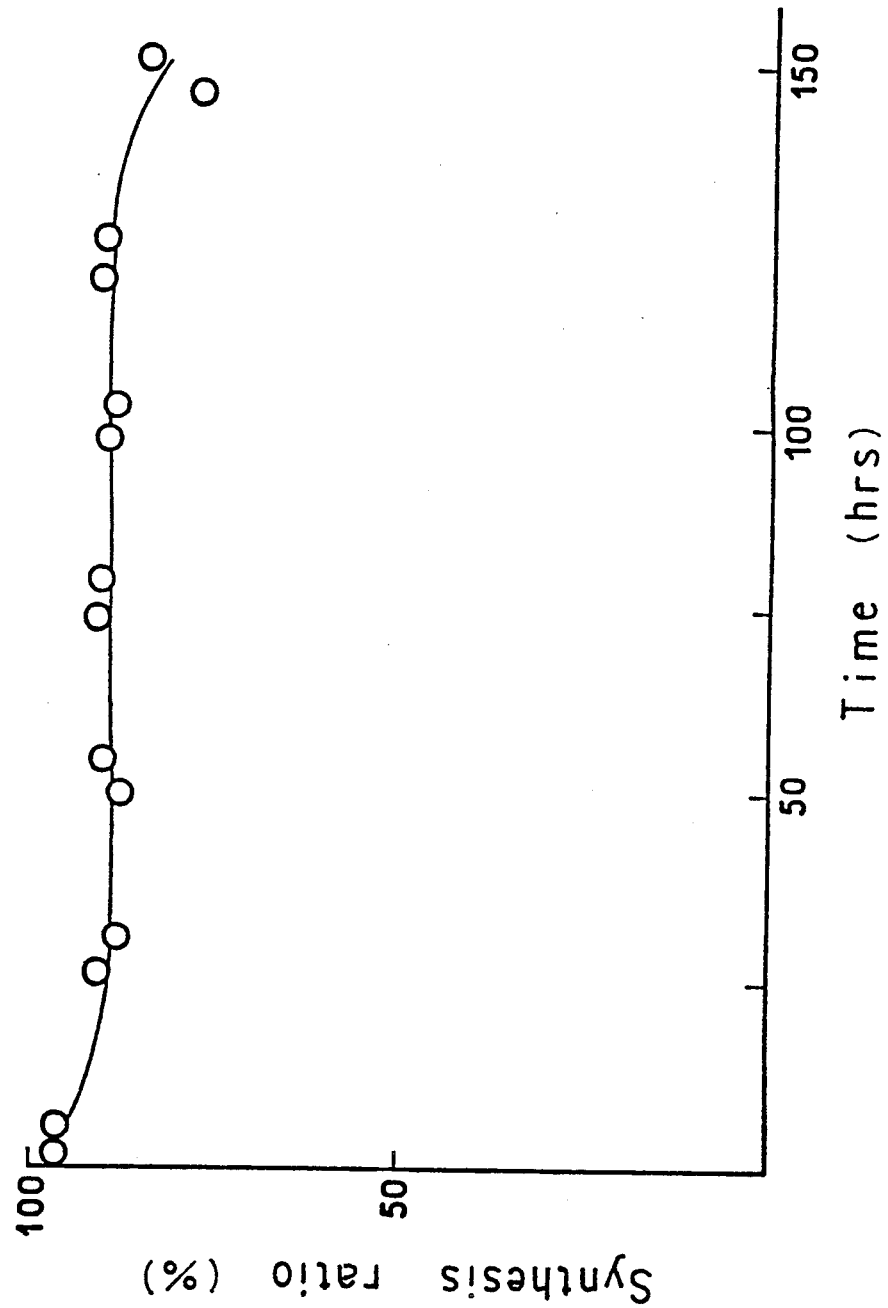
FIG. 2 is a graph of the data obtained from Example 15 of the synthesis ratio of the ester versus time.

The results thus obtained are shown in FIG. 2. In FIG. 2, the synthesis ratio of the ester (%) is on the ordinate and the time (hrs) after start of the reaction in the first run (zero hour) is on the abscissa, the ester synthesis ratio in each run as attained by allowing the newly charged substrates to react with each other for 3 hours being plotted against the time at which the substrate substitution was conducted. During the period from the determination of the ratio to substrate substitution, the reaction mixture was allowed to stand while the enzyme and substrates were in contact with one another.

FIG. 2 indicates that the ester synthesis ratio after 130 hours is still not less than 90% and accordingly that the enzyme does not loss its activity at all at least in its repeated use in 14 reaction runs (or about 43 times if it is supposed that the reaction run is repeated in 3-hour cycles).

EXAMPLE 16

The procedure of Example 15 was followed except that the reaction mixture was composed of 100 mg of cholesterol, 220 mg of oleic acid, 2 ml of isooctane, 8 ml of water and 500 U (16.7 mg) of lipase MY.

Figure 3:
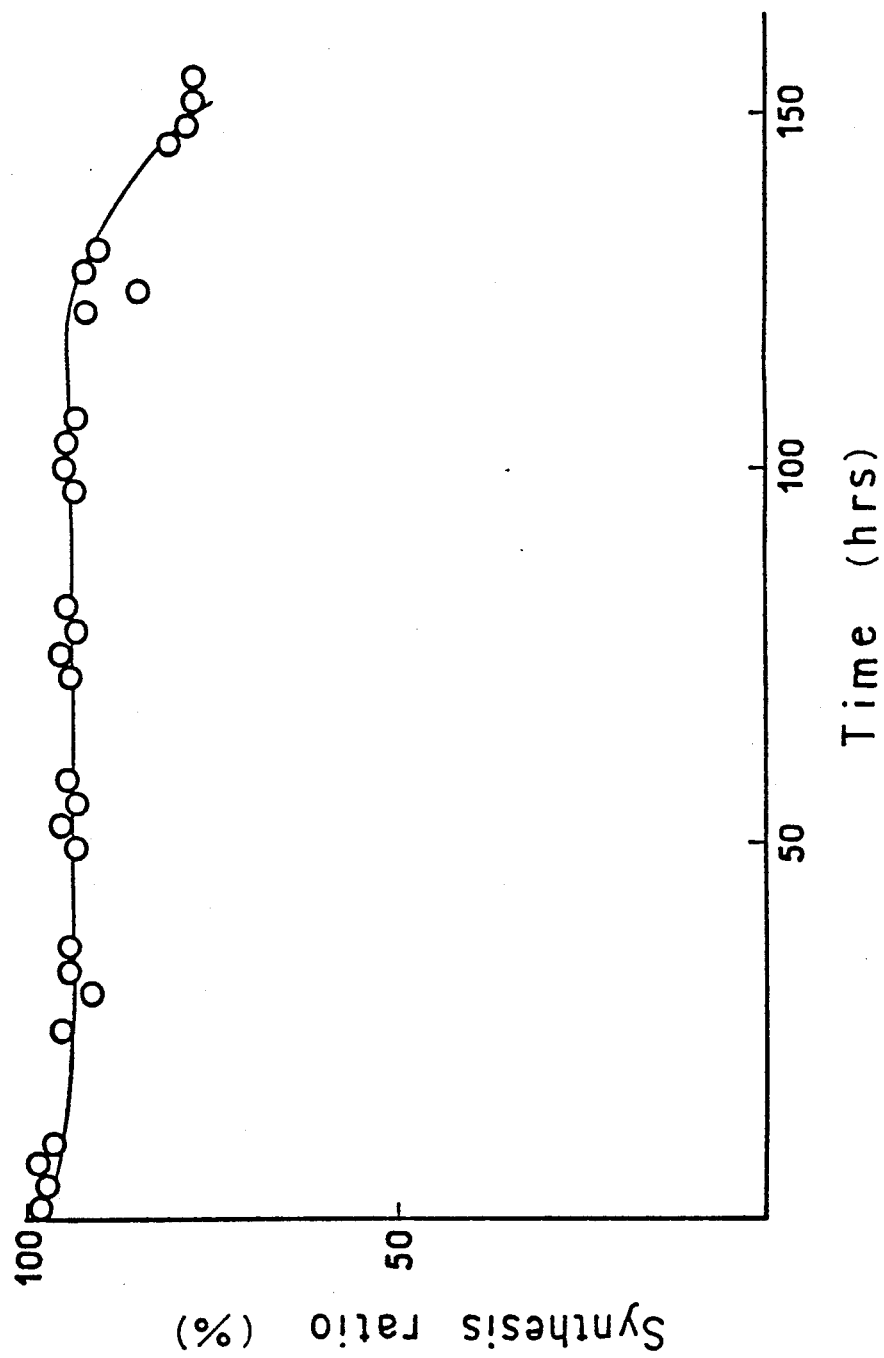
FIG. 3 is a graph plotted in the same manner as FIG. 2, showing the results of the data obtained from Example 16.

The results obtained are shown in FIG. 3 in the same manner as in FIG. 2.

From FIG. 3, it is seen that at least 94% synthesis ratio can be secured in each repeated 3-hour reaction run until about 130 hours, namely the synthesis reaction can be repeated about 28 times, without enzyme losses due to substitution of the organic solvent phase.

EXAMPLE 17

A mixture of 100 mg of cholesterol and 220 mg of oleic acid was treated for 18 hours with 0.5 ml of an aqueous solution of 500 U of lipase MY with water added to the system in an amount of 0.5–10.0 ml.

After reaction, 10 ml of isooctane was added to the reaction mixture and the resulting mixture was allowed to stand. The upper isooctane layer, except the interface portion, was removed, 100 mg of cholesterol and 220 mg of oleic acid were newly added to the lower enzyme solution layer, and the reaction was conducted for 18 hours. The above procedure was repeated three times in all.

The results obtained are given below in Table 12.

TABLE 12

| Run No. | Amount of water added (ml) | Synthesis ratio (%) 1st reaction | 2nd reaction | 3rd reaction |
|---|---|---|---|---|
| 1 | 0 | 87.5 | 86.8 | 87.0 |
| 2 | 0.5 | 97.6 | 97.3 | 97.4 |
| 3 | 1.0 | 97.4 | 97.4 | 97.3 |
| 4 | 2.0 | 98.2 | 98.0 | 97.9 |
| 5 | 4.0 | 97.4 | 97.0 | 96.8 |
| 6 | 6.0 | 96.9 | 96.8 | 96.9 |
| 7 | 10.0 | 92.7 | 92.0 | 92.0 |

In this example, the reaction was carried out in an aqueous system, then the system was converted to a water-isooctane system and, after separation of the enzyme, this was re-used in an aqueous system. The data shown above in Table 12 clearly indicate that even when the amount of water in the reaction system is large, the equilibrium of reaction shifts in the direction toward synthesis, that the enzyme can be separated with ease by converting the system to a water-organic solvent two-phase system after reaction, and further that the thus-separated enzyme can be used repeatedly without losses in its activity. The above results also indicate that even when cholesterol remains partly undissolved in the system, the synthesis reaction can proceed to a satisfactory extent.

EXAMPLE 18

The reaction was carried out in a reaction system composed of 100 mg of cholesterol, 220 mg of one of various fatty acids, 500 U of lipase MY and 10 ml of isooctane. Thereafter, 3 ml of water was added and the mixture was stirred, followed by phase separation as a water-isooctane two-phase system. The isooctane layer, except the interface portion, was removed, a substrate solution composed of 100 mg of cholesterol, 220 mg of the fatty acid and 10 ml of isooctane was added newly to the remaining aqueous enzyme solution and the reaction was conducted for 18 hours.

The above procedure was repeated three times in all. The results obtained are shown below in Table 13.

TABLE 13

| Run No. | Fatty acid | Synthesis ratio (%) | | |
|---|---|---|---|---|
| | | 1st reaction | 2nd reaction | 3rd reaction |
| 1 | B-1 | 88.9 | 98.6 | 98.7 |
| 2 | B-2 | 99.0 | 98.8 | 98.8 |
| 3 | B-3 | 98.5 | 98.0 | 98.4 |

In this example, the reaction was performed in a water-containing organic solvent system and, then, the enzyme was separated after conversion to a water-organic solvent two-phase system and re-used. From Table 13 given above, it is understood that the reaction can readily proceed and the conversion of the system after reaction to a water-organic solvent two-phase system by addition of water results in easy phase separation, whereby the enzyme can be recovered and re-used.

EXAMPLE 19

The reaction mixture as obtained in Example 18 after the first reaction was filtered, without addition of 3 ml of water, through a 0.45 $\mu$m Teflon membrane filter. The lipase MY used (powder) remained undissolved, adhering to the reaction vessel wall or forming blocks, but could be recovered by washing of the reaction vessel with two 10-ml portions of isooctane, followed by filtration.

The enzyme recovered, together with the membrane filter, was transferred to the same reaction vessel, the same substrate solution as used in Example 18 was added, and the reaction was again conducted for 18 hours. This procedure was repeated three times. The results obtained are shown below in Table 14.

TABLE 14

| Run No. | Fatty acid | Synthesis ratio (%) | | |
|---|---|---|---|---|
| | | 1st reaction | 2nd reaction | 3rd reaction |
| 1 | B-1 | 98.9 | 98.5 | 98.3 |
| 2 | B-2 | 99.0 | 98.7 | 98.9 |
| 3 | B-3 | 98.5 | 97.8 | 98.0 |

In this example, the enzyme was separated by using a membrane filter and re-used. The data in Table 14 indicate that the enzyme in a dispersed state can be recovered for reuse by filtration.

EXAMPLE 20

To a substrate solution composed of 100 mg of cholesterol, 220 mg of oleic acid and 10 ml of isooctane was added 500 U (16.7 mg) of lipase MY in powder form, and the reaction was conducted for 18 hours. The reaction mixture was centrifuged at 8,000 rpm for 10 minutes to thereby cause the suspended enzyme particles to precipitate. The supernatant was removed by decantation, the enzyme particles were returned to the same reaction vessel as before and, after addition of a new portion of the substrate solution, the synthesis reaction was repeated.

The above synthesis reaction procedure was repeated three times in all. The synthesis ratio was 8.5% in the first reaction, 97.3% in the second and 6.8% in the third.

This example, in which the synthesis reaction was conducted in a water-containing organic solvent system and the enzyme was separated from the reaction mixture by centrifugation and re-used, shows that the enzyme suspended in the reaction system can be recovered for reuse by centrifugation.

EXAMPLE 21

To a substrate solution composed of 100 mg of cholesterol, 200 mg of $\alpha$-hydroxypalmitic acid and 2 ml of isooctane was added an aqueous solution of 1,000 U (33.3 mg) of lipase MY in 8 ml of water, and the reaction was carried out for 72 hours. After reaction, the emulsified upper layer portion of the reaction mixture was filtered portionwise using a polypropylene-made hydrophobic porous membrane "Duraguard #2400" (porosity 38%, maximum pore size 0.02×0.2 $\mu$m, critical surface tension 35 dyne/cm, product of Polyplastics Co.) The aqueous enzyme solution could not wet the surface of said membrane because of its higher surface tension than the critical surface tension of the above membrane and accordingly could not pass through the micropores occurring on the membrane surface whereas isooctane permeated the micropores.

The nonpermeating aqueous enzyme solution was returned to the reaction vessel and, after newly adding thereto the same substrate solution as above, the reaction was conducted again for 72 hours.

The synthesis ratio in the above-mentioned first reaction was 73.2% and that in the second reaction was 69.5%.

This example, in which the reaction was conducted in a water-organic solvent two-phase system and the reaction mixture was filtered using a hydrophobic porous membrane for selective permeation of the organic solvent, shows that the aqueous enzyme solution can be separated from the somewhat emulsified reaction mixture as well by utilizing the surface tension-based selective permeability of the membrane.

EXAMPLE 22

Using an alcohol component (used in an amount of 100 mg) given in Table 15 together with a fatty acid and an enzyme each given in the same table each in a specified amount and employing the reaction system and reaction time given in said table, the reaction was performed, and the aqueous enzyme solution was separated from the organic solvent phase containing the desired ester and unreacted substrates in the same manner as in Example 15. In this manner, the synthesis reaction was repeated using the enzyme repeatedly. The results obtained are also shown in Table 15. In the table, "PB" means 0.05 M phosphate buffer (pH 7.0).

TABLE 15(1)

| Run No. | Enzyme (U) | Alcohol | Fatty acid (moles based on alcohol) | PB (ml) | Organic solvent (ml) | Time (hr) |
|---|---|---|---|---|---|---|
| 1 | E-1 ( 500) | A-1 | B-3 (3) | 8 | S-2 (2) | 18 |
| 2 | E-1 ( 500) | A-1 | B-4 (3) | 8 | S-2 (2) | 18 |
| 3 | E-1 (1000) | A-1 | B-8 (3) | 8 | S-2 (2) | 18 |
| 4 | E-1 (1000) | A-1 | B-12(3) | 8 | S-2 (2) | 45 |
| 5 | E-1 (1000) | A-1 | B-6 (3) | 8 | S-2 (2) | 48 |
| 6 | E-1 ( 500) | A-2 | B-1 (3) | 8 | S-2 (2) | 18 |
| 7 | E-1 ( 500) | A-3 | B-1 (3) | 8 | S-2 (2) | 18 |
| 8 | E-1 ( 500) | A-4 | B-1 (3) | 8 | S-2 (2) | 18 |
| 9 | E-1 ( 500) | A-5 | B-1 (3) | 8 | S-2 (2) | 18 |
| 10 | E-1 ( 500) | A-6 | B-1 (3) | 8 | S-2 (2) | 18 |
| 11 | E-2 (1000) | A-1 | B-1 (3) | 8 | S-2 (2) | 18 |
| 12 | E-3 (1000) | A-1 | B-1 (3) | 8 | S-2 (2) | 18 |
| 13 | E-5 ( 500) | A-1 | B-1 (3) | 8 | S-2 (2) | 18 |
| 14 | E-1 ( 500) | A-1 | B-1 (3) | 8 | S-3 (2) | 18 |
| 15 | E-1 ( 500) | A-1 | B-1 (3) | 8 | S-4 (2) | 18 |
| 16 | E-1 ( 500) | A-1 | B-1 (3) | 8 | S-5 (2) | 18 |
| 17 | E-1 ( 500) | A-1 | B-1 (3) | 8 | S-6 (2) | 18 |
| 18 | E-1 ( 500) | A-1 | B-1 (3) | 8 | S-1 (2) | 18 |
| 19 | E-1 (1000) | A-9 | B-8 (1.2) | 8 | S-2 (2) | 5 |
| 20 | E-1 (1000) | A-9 | B-3 (1.2) | 8 | S-2 (2) | 5 |
| 21 | E-1 (1000) | A-9 | B-1 (1.2) | 8 | S-2 (2) | 5 |
| 22 | E-1 (1000) | A-9 | B-13(1.2) | 8 | S-2 (2) | 5 |
| 23 | E-1 (1000) | A-9 | B-6 (1.2) | 8 | S-2 (2) | 24 |
| 24 | E-1 (1000) | A-8 | B-8 (1.2) | 8 | S-2 (2) | 24 |
| 25 | E-1 (1000) | A-8 | B-3 (1.2) | 8 | S-2 (2) | 24 |
| 26 | E-1 (1000) | A-8 | B-1 (1.2) | 8 | S-2 (2) | 5 |
| 27 | E-1 (1000) | A-8 | B-13(1.2) | 8 | S-2 (2) | 5 |
| 28 | E-1 (1000) | A-8 | B-6 (1.2) | 8 | S-2 (2) | 24 |
| 29 | E-1 (1000) | A-7 | B-3 (1.2) | 8 | S-2 (2) | 72 |
| 30 | E-1 (1000) | A-7 | B-1 (1.2) | 8 | S-2 (2) | 72 |
| 31 | E-1 (1000) | A-7 | B-13(1.2) | 8 | S-2 (2) | 72 |

TABLE 15(2)

| Run No. | Synthesis ratio (%) | | | | |
|---|---|---|---|---|---|
| | 1st | 2nd | 3rd | 4th | 5th |
| 1 | 98.5 | 98.5 | 98.4 | 98.3 | 98.2 |
| 2 | 96.5 | 95.8 | 96.1 | 95.7 | 96.3 |
| 3 | 94.3 | 94.1 | 94.2 | 93.8 | 93.9 |
| 4 | 91.0 | 90.7 | 88.4 | — | — |
| 5 | 85.5 | 86.0 | 80.1 | — | — |
| 6 | 95.4 | 95.6 | 95.1 | 94.8 | 94.9 |
| 7 | 69.3 | 69.0 | 70.7 | 67.9 | 69.0 |
| 8 | 92.8 | 94.7 | 93.1 | 90.9 | 92.5 |
| 9 | 55.3 | 56.0 | 55.8 | 55.3 | 56.0 |
| 10 | 70.5 | 70.3 | 71.4 | 69.1 | 70.2 |
| 11 | 85.3 | 87.0 | 84.8 | 83.6 | 85.1 |
| 12 | 55.2 | 56.5 | 56.4 | 55.3 | 55.2 |
| 13 | 97.7 | 97.9 | 96.8 | 97.3 | 97.5 |
| 14 | 96.8 | 96.7 | 96.7 | 96.8 | 96.8 |
| 15 | 96.7 | 96.8 | 96.7 | 96.6 | 96.5 |
| 16 | 96.5 | 96.5 | 96.7 | 96.6 | 96.5 |
| 17 | 96.0 | 96.2 | 96.0 | 96.1 | 96.3 |
| 18 | 96.5 | 96.4 | 96.4 | 96.5 | 96.4 |
| 19 | 86.7 | 87.2 | 88.4 | 85.0 | 87.4 |
| 20 | 84.3 | 85.1 | 83.7 | 85.8 | 84.4 |
| 21 | 96.9 | 95.0 | 95.5 | 94.9 | 94.8 |
| 22 | 96.9 | 95.2 | 94.9 | 95.9 | 96.1 |
| 23 | 87.9 | 86.0 | 89.7 | 87.8 | 86.0 |
| 24 | 64.7 | 65.4 | 63.4 | — | — |
| 25 | 97.9 | 98.2 | 97.0 | — | — |
| 26 | 94.5 | 95.6 | 97.6 | — | — |
| 27 | 89.9 | 92.3 | 90.4 | — | — |
| 28 | 94.2 | 93.8 | 94.3 | — | — |
| 29 | 79.1 | 78.2 | — | — | — |
| 30 | 94.3 | 94.2 | — | — | — |
| 31 | 95.9 | 94.3 | — | — | — |

The data in Table 15 indicate that, in the water-organic solvent two-phase system, the separation and reuse of the enzyme is possible for all the combinations of various alcohols, fatty acids, enzymes and organic solvents as used, with little enzyme losses caused by repeated enzyme use.

EXAMPLE 23

Figure 4:
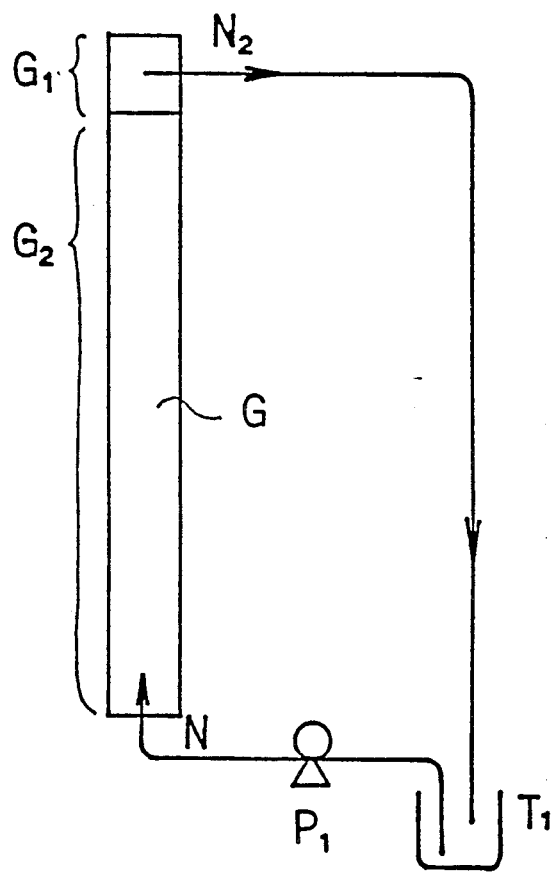
FIG. 4 is a flow chart which is described in Example 23.

Using an apparatus for continuous reaction comprising a glass column (G), 2 cm in inside diameter and 2 m in length, a pump (P1) and a receptacle (T1), as shown by the flowchart given in FIG. 4, a portion (G2) of the column was filled with 600 ml of an aqueous solution of lipase MY in 0.05 M phosphate buffer (pH 7.0) having an enzyme concentration of 125 U/ml, and a substrate solution composed of 2,500 mg of cholesterol, 2,500 mg of oleic acid and 250 ml of isooctane was introduced into the aqueous enzyme solution layer portion (G2) at a flow rate of 9.5 ml/min by means of the pump (P1) in the form of small oily droplets through a nozzle (N1) disposed at the bottom of the column (G).

The small droplets introduced rose through the aqueous enzyme solution layer to the force of injection and the bouyancy while undergoing the reaction and separated as an isooctane layer containing the reaction product at an upper portion (G1) of the glass column.

This isooctane layer was allowed to overflow through a nozzle (N2) and again fed to the aqueous enzyme solution layer (G2) through the receptacle (T1) by means of the pump (P1).

In this manner, the reaction was conducted while recycling the substrate solution through the aqueous enzyme solution repeatedly. The changes of the ester synthesis ratio with time as measured are shown in FIG. 5.

Figure 5:
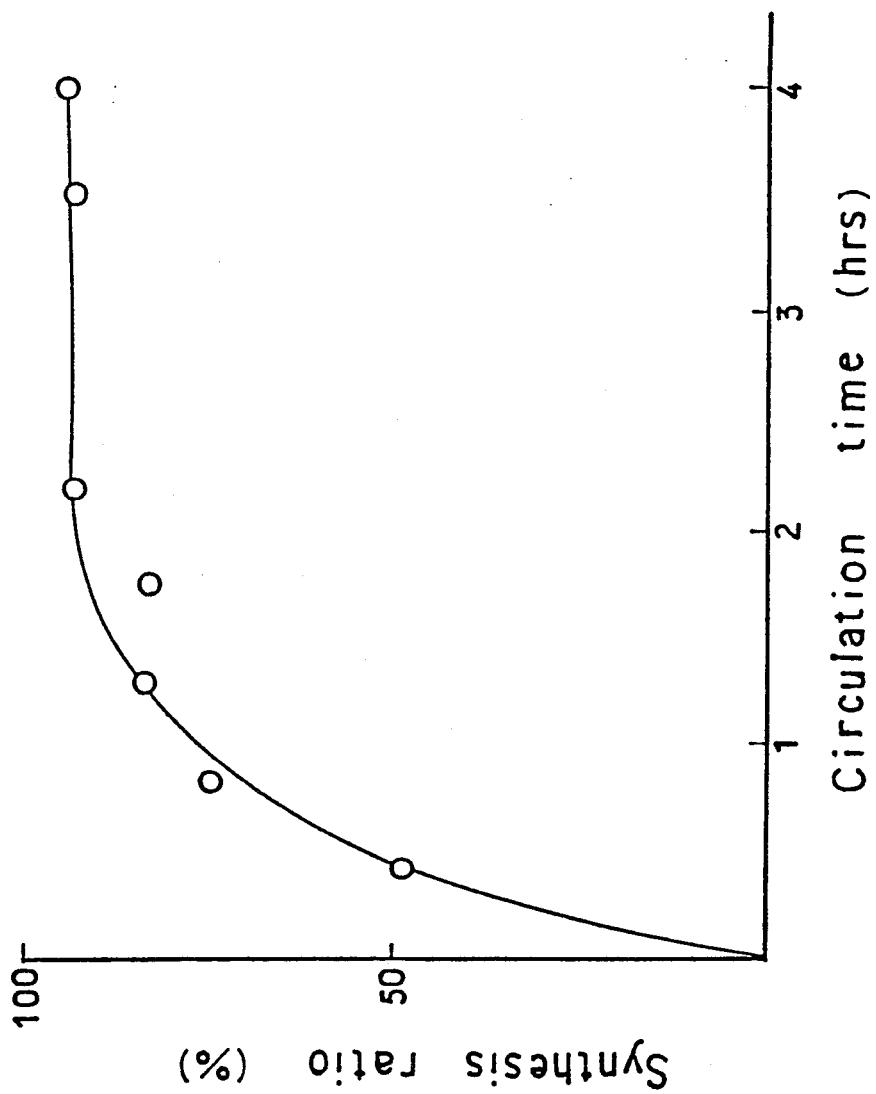
FIG. 5 is a graph of data obtained from Example 23, showing the changes of the ester synthesis ratio with time.

In FIG. 5, the synthesis ratio (%) is on the ordinate and the circulation time (hrs) on the abscissa, the ratios as determined for samples taken from the reaction mixture flowing into the receptacle (T1) at timed intervals being plotted against the corresponding circulation times.

FIG. 5 shows that the ratio reaches 95%, or an almost equilibrium state, in about 4 hours. It is also indicated that since the rate of feeding to the column is 9.5 ml/min, it takes about 26.3 minutes for the whole 250-ml substrate solution to contact once with the aqueous enzyme solution and that about 9 times of circulation drives the reaction to an equilibrium. The number of times of circulation naturally varies depending on such factors as the manner of formation and extinction of droplets and the retention time and said number can be varied by using column packings, baffle plates, stirring, etc.

EXAMPLE 24

Figure 6:
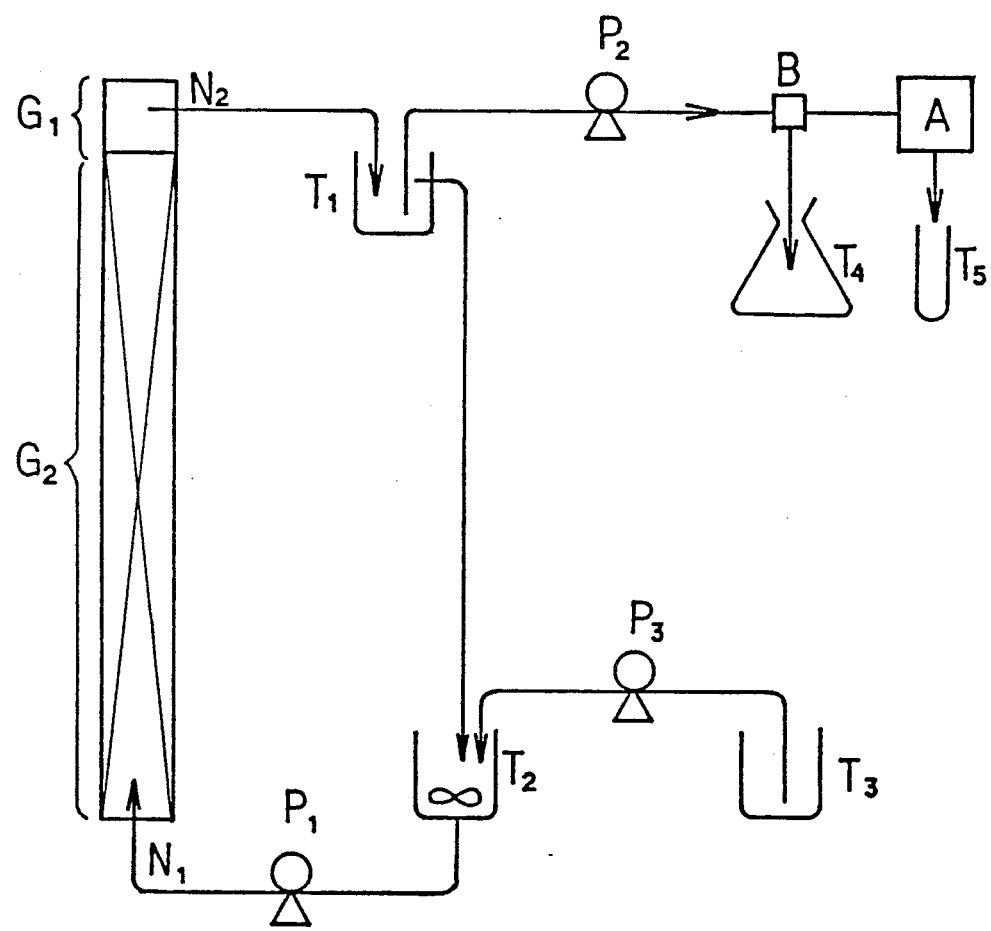
FIG. 6 is a flow chart which is described in Example 24.

Using a continuous reaction vessel comprising glass column (G), 2 cm in inside diameter and 2 m in length, pumps (P1, P2, P3), a distributor (B), autosampler (A), receptacle (T1), mixing vessel (T2), raw material tank (T3), reaction mixture tank (T4) and reaction terminator-containing test tube (T5), as shown by the flowchart in FIG. 6, a portion (G2) of the column was filled with 600 ml of a solution of lipase MY in phosphate buffer (pH 7.0) having an enzyme concentration of 125 U/ml, and a substrate solution composed of 2,000 mg of cholesterol, 3,000 mg of oleic acid and 600 ml of isooctane was introduced into the aqueous enzyme solution layer portion (G2) in the form of small oily droplets through a nozzle (N1) disposed at the bottom of the column at a rate of 15.5 ml/min by means of the pump (P1).

The small droplets introduced flew up through the aqueous enzyme solution layer to the force of injection and the bouyancy while undergoing the reaction to form an isooctane layer containing the reaction product at an upper portion (G1) of the glass column. This isooctane layer was allowed to overflow through a nozzle (N2) and retained in the receptacle (T1) temporarily and partly withdrawn continuously into the reaction mixture tank (T4) via the distributor (B) at a rate of 0.25 ml/min by means of the pump (P2).

The remaining portion of the isooctance solution as overflowing from the receptacle (T1) was introduced into the mixing tank (T2) and mixed therewith a new substrate solution portion having the same composition as above and supplied from the raw material tank (T3) at a rate of 0.25 ml/min by means of the pump (P3). The resulting mixed substrate solution was again fed to the (G2) portion of the glass column through the nozzle (N1) at a rate of 15.5 ml/min by means of the pump (P1).

The autosampler (A) sampled the reaction mixture from the distributor (B) at 3-hour intervals and transferred the samples to the test tube (T5) containing a reaction terminator solution (acetone/ethanol=1/1).

In this manner, the reaction was effected by recycling the substrate solution through the aqueous enzyme solution repeatedly while the reaction mixture was sampled at 3-hour intervals by means of the autosampler (A) and assayed for the ester synthesis ratio. The thus-obtained data are shown in FIG. 7.

Figure 7:
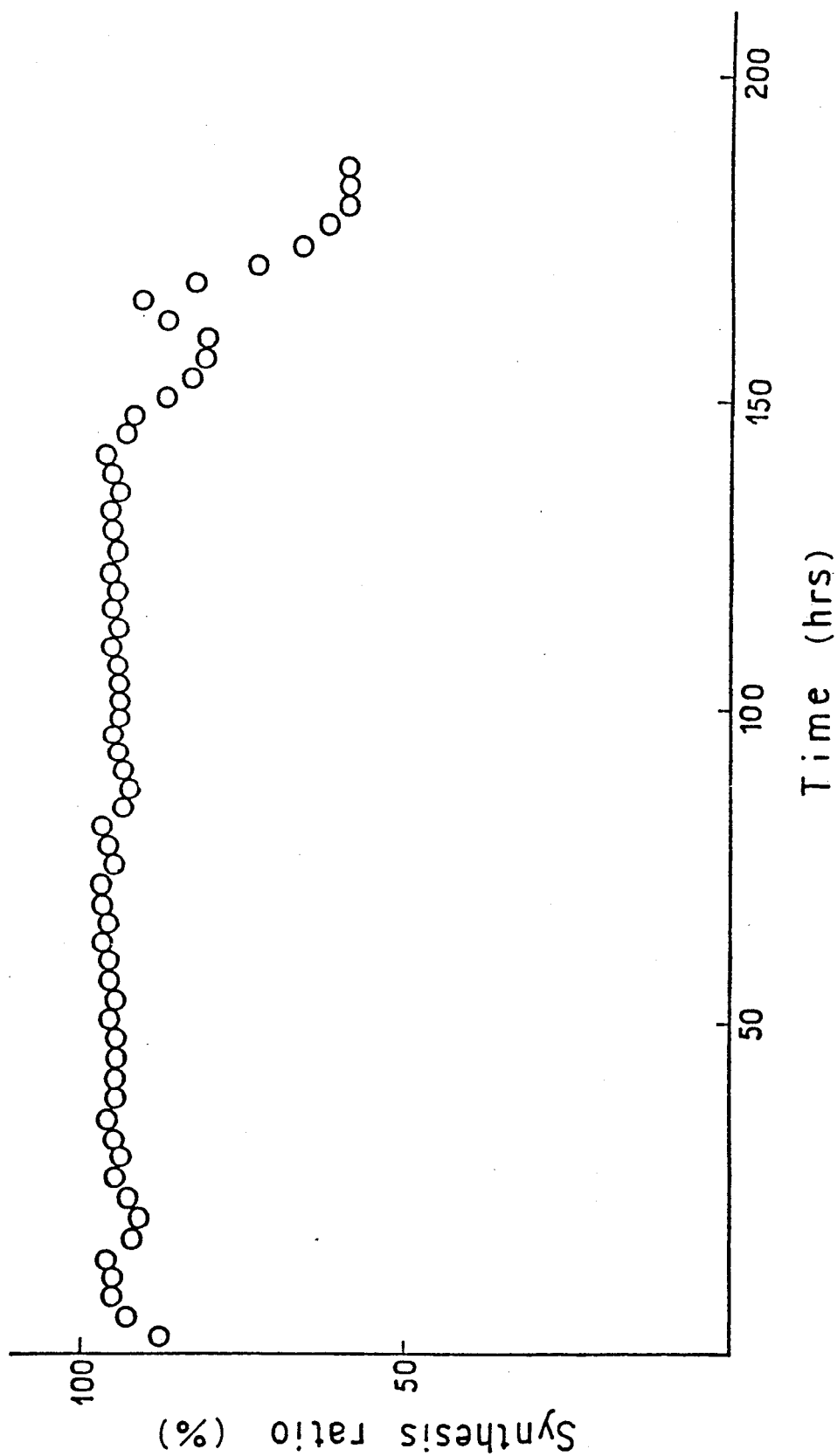
FIG. 7 is a graph of results obtained from Example 24, showing the synthesis ratio plotted against time.

In FIG. 7, the synthesis ratio (%) is on the ordinate and the time (hrs) from the start of reaction (zero hour) is on the abscissa, the ratio being plotted against the time.

During the period from the start of reaction to about 2 hours after that, the isooctane layer in the upper part (G1) of the column was in an emulsified state but began to show phase separation with the progress of reaction and the separation was complete at about 5 hours.

FIG. 7 shows that when a water-organic solvent system is used as the reaction system, emulsification does not occur even in a simple spray column such as the one shown in FIG. 6 but that the desired ester can be synthesized continuously using the enzyme repeatedly without exchange or supplementation of the enzyme for 150 hours or longer, while the synthesis ratio can be maintained at 95% or more.

EXAMPLE 25

A vessel was divided into two compartments, an upper and a lower, by means of a polypropylene-made hydrophobic membrane ["Duraguard 2500", product of Polyplastics Co., thickness 25 μm, average pore size 0.1 μm, maximum pore size 0.04×0.4 μm, porosity 45%, effective surface area (membrane area minus area required for fitting the vessel with the membrane) 9.6 cm$^2$]. The lower compartment (50 cm$^3$ in capacity) was filled with 50 cm$^3$ of an aqueous solution of lipase MY having an enzyme concentration of 62.5 U/ml. A communicating tube connected to said compartment was also filled with the same aqueous enzyme solution so that the liquid level was higher by 20 cm than the membrane level.

The upper compartment of the above vessel was charged with a substrate solution composed of 20 mg of cholesterol, 44 mg of oleic acid and 10 ml of isooctane. The whole vessel was shaken on a skaker at a stroke of 6 cm and a frequency of 120 cpm to thereby effect the reaction.

The synthesis ratio after 18 hours of reaction was 94.6%. The reaction system was not emulsified. No penetration of water into the substrate phase was observed.

When the reaction is effected in the above manner by contacting the enzyme and substrates with one another through a porous reaction membrane, the aqueous enzyme solution, which has a high surface tension, cannot wet the hydrophobic membrane nor pass through micropores of said membrane, hence is not mixed with the hydrophobic substrates in the substrate solution. On the contrary, the hydrophobic substrates penetrate micropores of the hydrophobic membrane and come into contact with that portion of enzyme which is absorbed on said hydrophobic interface on the lower side of the membrane. In this case, an increase in the frequency of contact among the enzyme and substrates results in a shortened reaction time. Therefore, the use of a crepe, spiral, tubular, hollow fiber or like appropriate type in lieu of the flat membrane type such as mentioned above serves to further reduce the reaction time.

EXAMPLE 26

A membrane "Duraguard 3501" (product of the same company as above, the thickness, pore size and porosity being the same as above) which is hydrophilic as a result of surface treatment was used in place of the "Duraguard 2500" used in Example 25. The upper and lower compartments divided by said membrane were charged respectively with the same substrate solution and enzyme solution as above. The liquid level in the communicating tube was the same as the membrane level.

The reaction was conducted for 18 hours in the same manner as in Example 25. The reaction system was not emulsified, and the synthesis ratio was 92.0%.

When a hydrophilic membrane is used as in this example, the aqueous membrane and contacts with the substrates in the upper part of the membrane and catalyzes the reaction there.

EXAMPLE 27

The procedure of Example 25 was followed using 4 kinds of membrane as shown in Table 16. The volume of the lower compartment was 4 cm$^3$ and other reaction conditions were the same as in Example 25. The results obtained are also shown in Table 16.

TABLE 16

| Run No. | 1 | 2 | 3 | 4 |
|---|---|---|---|---|
| Membrane material | Regenerated cellulose | Teflon | Nitrocellulose | Nitrocellulose |
| Average pore size (μm) | 0.45 | 0.5 | 0.45 | 3.0 |
| Level difference between communicating tube and membrane (cm) | 0 | 30 | 0 | 0 |
| Reaction time (hrs) | 120 | 23 | 23 | 23 |
| Synthesis ratio (%) | 63.2 | 80.7 | 70.2 | 85.4 |
| Emulsification | None | None | None | None | the data in Table 16 indicate that the synsthesis reaction proceeds smoothly with every membrane used without emulsification of the reaction system.

EXAMPLE 28

The same membrane as used in Example 25 was used (except that the effective membrane area was 102 cm$^2$). The lower, compartment had a capacity of 82 cm$^3$ and was filled with an aqueous solution of lipase MY having a concentration of 62.5 U/ml. The liquid level in the communicating tube was 41 cm higher than the membrane level. The upper compartment was charged with a substrate solution composed of 400 mg of cholesterol, 880 mg of oleic acid and 40 ml of isooctane. A magnetic stirrer was placed on said membrane and revolved to thereby stir the substrate phase. The whole vessel was placed in a constant-temperature room and the reaction was performed for 24 hours. The results obtained are shown below in Table 17.

TABLE 17

| Run No. | Reaction time (hrs) | Synthesis ratio (%) | Run No. | Reaction time (hrs) | Synthesis ratio (%) |
|---|---|---|---|---|---|
| 1 | 1 | 10.0 | 2 | 2 | 22.8 |
| 3 | 3 | 38.7 | 4 | 4 | 51.2 |
| 5 | 5 | 61.7 | 6 | 6 | 70.8 |
| 7 | 7 | 77.0 | 8 | 8 | 81.5 |
| 9 | 9 | 87.0 | 10 | 10 | 90.0 |
| 11 | 16 | 95.4 | 12 | 24 | 96.2 |

The results obtained above in Example 25-28 show that a larger membrane area allows a larger amount of the substrates to be subject to the synthesis reaction and that the effective membrane area is one of the important factors decisive of the synthesis velocity.

EXAMPLE 29

The same membrane as used in Example 25 was used (except that the effective membrane area was 10.3 cm$^2$). The lower compartment had a capacity of 4.1 cm$^3$ and was filled with an aqueous lipase MY solution in a varying concentration. The liquid level in the communicating tube was set at a level 41 cm higher than the membrane level, and the reaction was conducted in the same manner.

The synthesis ratio data after 3 hours are shown below in Table 18.

TABLE 18

| Run No. | Concentration of aqueous lipase solution (U/ml) | Synthesis ratio (%) |
|---|---|---|
| 1 | 600 | 64.8 |
| 2 | 300 | 65.3 |
| 3 | 200 | 65.2 |
| 4 | 100 | 63.2 |
| 5 | 62.5 | 46.4 |

The data in Table 18 suggest that the enzyme adsorption on the hydrophilic-hydrophobic interface reaches a suturation at about 200 U/ml.

EXAMPLE 30

Using an aqueous lipase MY solution (600 U/ml) and a substrate solution in which an alcohol component (100 mg) specified in Table 19 was combined with a fatty acid and an organic solvent each given in Table 19, the reaction was carried out in an appropriate reaction vessel with Duraguard 2500 used therein. The results obtained are also shown in Table 19, together with the reaction time data.

TABLE 19

| Run No. | Alcohol (100 mg) | Fatty acid (moles based on alcohol) | Organic solvent (ml) | Time (hr) | Synthesis ratio (%) |
|---|---|---|---|---|---|
| 1 | A-1 | B-1 (3) | S-2 (20) | 18 | 97.1 |
| 2 | A-1 | B-2 (3) | S-2 (20) | 18 | 97.8 |
| 3 | A-1 | B-3 (3) | S-2 (20) | 18 | 98.3 |
| 4 | A-1 | B-4 (3) | S-2 (20) | 18 | 96.0 |
| 5 | A-1 | B-8 (3) | S-2 (20) | 18 | 94.5 |
| 6 | A-1 | B-12(3) | S-2 (20) | 45 | 90.8 |
| 7 | A-1 | B-6 (3) | S-2 (20) | 48 | 86.0 |
| 8 | A-2 | B-1 (3) | S-2 (20) | 18 | 95.1 |
| 9 | A-3 | B-1 (3) | S-2 (20) | 18 | 69.0 |
| 10 | A-4 | B-1 (3) | S-2 (20) | 18 | 93.1 |
| 11 | A-5 | B-1 (3) | S-2 (20) | 18 | 55.8 |
| 12 | A-6 | B-1 (3) | S-2 (20) | 18 | 71.7 |
| 13 | A-9 | B-8 (1.2) | S-2 (20) | 5 | 87.2 |
| 14 | A-9 | B-3 (1.2) | S-2 (20) | 5 | 85.3 |
| 15 | A-9 | B-1 (1.2) | S-2 (20) | 5 | 95.8 |
| 16 | A-9 | B-13(1.2) | S-2 (20) | 5 | 95.1 |
| 17 | A-9 | B-6 (1.2) | S-2 (20) | 24 | 87.9 |
| 18 | A-8 | B-8 (1.2) | S-2 (20) | 24 | 66.5 |
| 19 | A-8 | B-3 (1.2) | S-2 (20) | 24 | 97.4 |
| 20 | A-8 | B-1 (1.2) | S-2 (20) | 5 | 94.7 |
| 21 | A-8 | B-13(1.2) | S-2 (20) | 5 | 90.0 |
| 22 | A-8 | B-6 (1.2) | S-2 (20) | 24 | 94.3 |
| 23 | A-7 | B-3 (1.2) | S-2 (20) | 72 | 78.3 |
| 24 | A-7 | B-1 (1.2) | S-2 (20) | 72 | 94.2 |
| 25 | A-7 | B-13(1.2) | S-2 (20) | 72 | 94.5 |
| 26 | A-1 | B-1 (3) | S-3 (20) | 18 | 96.8 |
| 27 | A-1 | B-1 (3) | S-4 (20) | 18 | 96.7 |
| 28 | A-1 | B-1 (3) | S-5 (20) | 18 | 96.4 |
| 29 | A-1 | B-1 (3) | S-6 (20) | 18 | 96.2 |
| 30 | A-1 | B-1 (3) | S-1 (20) | 18 | 96.4 |

In practicing the method, shown in Examples 25-30, continuous synthesis is possible by feeding the substrates (solution) to one of the compartments divided by a membrane while withdrawing the reaction mixture continuously.

EXAMPLE 31

In the first place, lipase MY was immobilized by mixing a resin for immobilization in the manner mentioned below in (1) or (2).

(1) One gram of ENTP-4000 (product of Kansai Paint Co., Ltd.) was mixed with 10 mg of benzoin ethyl ether and 40 mg of sorbitan monooleate. The mixture was melted completely by warming at 60° C. with stirring and then cooled to 4° C., 2,000 U of the enzyme in the powder form was added thereto, the resulting mixture was well kneaded, then diluted with 2 ml of isooctane and spread in the sheet form, 7 cm × 10 cm × 0.5 mm in size, and the sheet was covered with a transparent polyester film and gelled by illumination (a Toshiba chemical lamp used; 3 minutes). After gelation, the resin was cut to square pieces, 4-5 mm in side length and used as an immobilized enzyme preparation.

(2) The above procedure (1) was followed using benzene-heptane (1:1) in place of isooctane while omitting the use of sorbitan monooleate.

To each of the immobilized enzymes obtained above in (1) and (2) was added a substrate solution composed of 100 mg of cholesterol, 220 mg of oleic acid and 15 ml of isooctane with 3 ml of 0.05 M phosphate buffer (pH 7.0) thereto, and the reaction was conducted for 3 hours.

After reaction, the reaction mixture was filtered. To the immobilized enzyme thus recovered, there was newly added the same substrate solution as used above, and the reaction was carried out again.

The above reaction procedure was repeated five times in all. The results obtained are shown below in Table 20.

TABLE 20

| Run No. | Immobilized method | Synthesis ratio (%) | | | | |
|---|---|---|---|---|---|---|
| | | 1st | 2nd | 3rd | 4th | 5th |
| 1 | (1) | 97.7 | 94.8 | 96.5 | 95.4 | 96.8 |
| 2 | (2) | 96.5 | 97.0 | 96.3 | 94.8 | 95.4 |

EXAMPLE 32

1,000 U of lipase MY was mixed in advance with 100 mg of Celite and 0.1 ml of water to thereby cause adsorption of the enzyme on Celite. Thereafter, the mixture was made into an immobilized enzyme preparation by following the procedure (2) of Example 31.

The reaction was carried out for 4 hours using the above immobilized enzyme preparation and a reaction mixture composed of a substrate solution of 100 mg of cholesterol and 220 mg of oleic acid in 5 ml of isooctane, 10 ml of isooctane and 3 ml of 0.05 M phosphate buffer (pH 7.0) and the synthesis ratio was determined.

Thereafter, the reaction mixture was filtered and the immobilized enzyme thus separated was submitted to the same reaction again as an immobilized enzyme.

The above reaction procedure was repeated three times a day. On the third run, the synthesis ratio alone was determined while the reaction mixture was allowed to stand without filtration, with the immobilized enzyme and substrates coexisting in the system together with the product ester. Said mixture was filtered on the next day and subjected to new repetitions of the reaction procedure. In this manner, the reaction was continued for 10 days. The results obtained are shown in FIG. 8.

Figure 8:
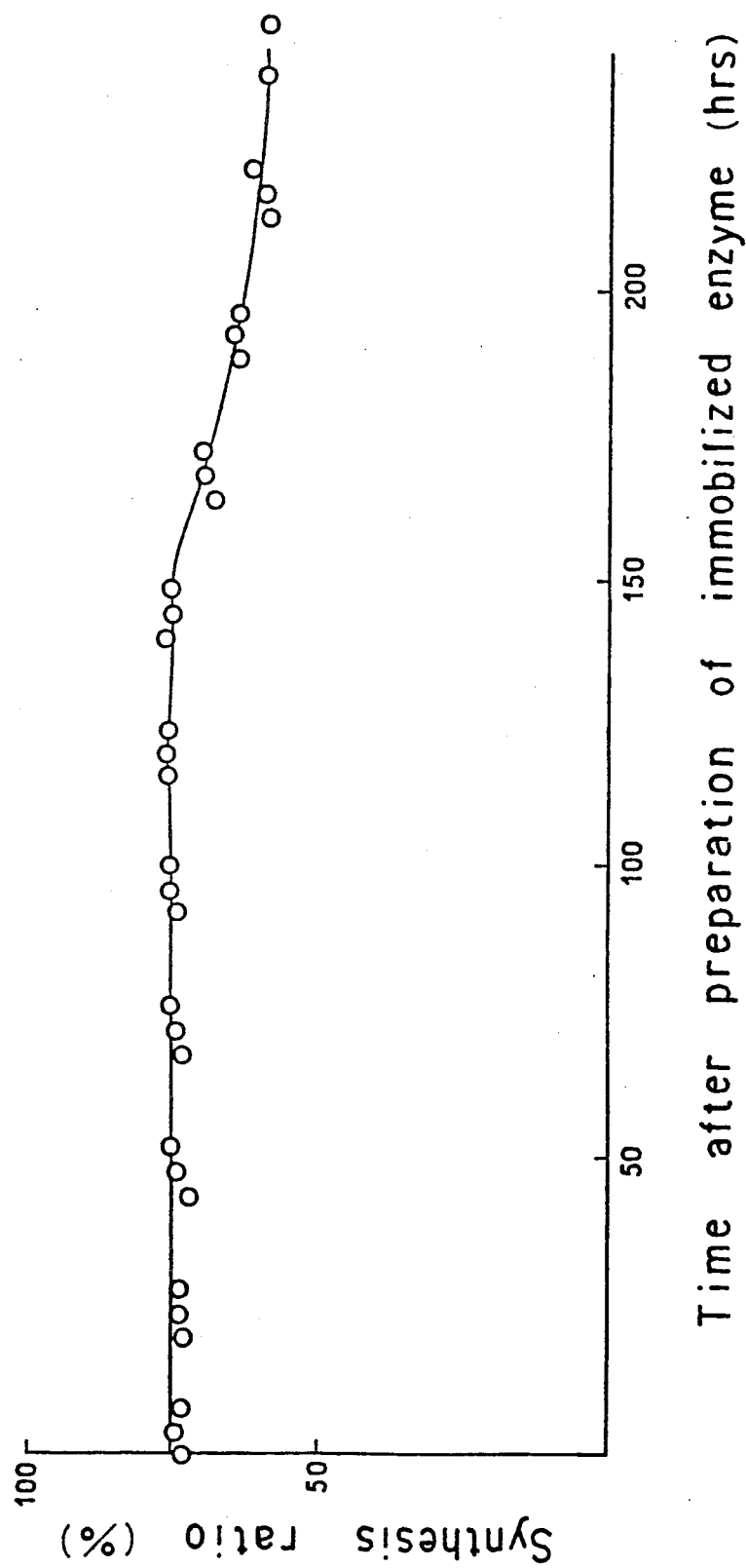
FIG. 8 is a graph of the results obtained from Example 32, showing the ester synthesis ratio plotted against the time after preparation of the immobilized enzyme.

In FIG. 8, the ester synthesis ratio is on the ordinate and the time after preparation of the immobilized enzyme on the abscissa, the ratio after 4 hours of reaction following the substrate replacement being plotted against the time.

It is evident from said figure that when an immobilized enzyme is used, the enzyme activity can be retained for at least 10 days and the reaction can be repeated accordingly.

EXAMPLE 33

An immobilized enzyme preparation was prepared from 2,000 U (19.0 mg) of cholesterol esterase T-18 (product of Toyo Jozo) by the procedure (2) of Example 31.

To the immobilized enzyme preparation were added 10 mg of cholesterol, 220 mg of oleic acid and 15 ml of isooctane, and the reaction was carried out for 1 hour. After reaction, the reaction mixture was filtered and the thus-recovered immobilized enzyme was used for the next run in the same reaction system as in the first run. In this manner, the reaction was repeated 36 times in all over 12 days. The synthesis ratio in the 36th run was 93.5%.

Thereafter, th reaction mixture was filtered once a day except holidays and, using the recovered immobilized emzyme, the same reaction was repeated for further 120 days in the same reaction system while replacing the substrate solution with a new one each day. A synthesis ratio of 95.0% was obtained 5 hours after the start of reaction on the final day.

EXAMPLE 34

Using the procedure of Example 32, 2,000 U (7.1 mg) of *Chromobacterium viscosum*-derived lipase ("Lipase T-01", product of Toyo Jozo) was made up into an immobilized enzyme preparation.

To the immobilized enzyme preparation were added a substrate solution composed of 100 mg of cholesterol, 220 mg of oleic acid and 15 ml of isooctane and 3 ml of 0.05 M phosphate buffer (pH 7.0), and the reaction was effected for 48 hours. After reaction, the reaction mixture was filtered and the immobilized enzyme thus recovered was used for the next reaction run in the same system as in the first run. The reaction was repeated three times in this manner. The synthesis ratio in the third run was 87.8%.

EXAMPLE 35

An immobilized enzyme preparation was prepared by immobilizing lipase MY on ENTP-4000 in a proportion of 2,000 U of enzyme per gram of resin by the procedure (1) of Example 31.

The reaction was carried out using a specified amount of the above immobilized enzyme preparation and a combination of an alcohol component, fatty acid and organic solvent each specified in Table 21. After reaction, the reaction mixture was filtered and the immobilized enzyme thus recovered was repeatedly used for the reaction, which was carried out in the same reaction system as in the first reaction.

The results obtained are shown in Table 21.

In Table 21, the indication "Note 1" for the reaction system means that said reaction system was a system in which the solvent system was composed of 15 ml of isooctane and 3 ml of 0.05 M phosphate buffer (pH 7.0).

TABLE 21

| Run No. | Enzyme (U) | Alcohol | Fatty acid (moles based on alcohol) | Reaction system | Time (hrs) | Synthesis ratio (%) | | |
|---|---|---|---|---|---|---|---|---|
| | | | | | | 1st | 2nd | 3rd |
| 1 | 2000 | A-1 | B-1 (3) | Note 1 | 18 | 97.7 | 96.8 | 97.0 |
| 2 | " | " | B-2 (3) | " | " | 98.7 | 96.7 | 98.5 |
| 3 | " | " | B-3 (3) | " | " | 98.4 | 97.5 | 97.9 |
| 4 | " | " | B-4 (3) | " | " | 96.0 | 96.0 | 96.4 |
| 5 | " | " | B-8 (3) | " | " | 94.0 | 94.8 | 95.3 |
| 6 | " | " | B-12(3) | " | " | 85.6 | 83.9 | 87.3 |
| 7 | " | " | B-6 (3) | " | " | 56.0 | 57.1 | 56.5 |
| 8 | " | A-2 | B-1 (3) | " | " | 95.1 | 94.8 | 96.2 |
| 9 | " | A-3 | " | " | " | 68.8 | 69.5 | 67.8 |
| 10 | " | A-4 | " | " | " | 93.2 | 94.3 | 93.8 |
| 11 | " | A-5 | " | " | " | 55.7 | 56.7 | 56.0 |
| 12 | " | A-6 | " | " | " | 71.3 | 70.7 | 70.9 |
| 13 | 4000 | A-9 | B-8 (1.2) | " | 5 | 87.3 | 87.8 | 87.1 |
| 14 | " | " | B-3 (1.2) | " | " | 85.1 | 86.2 | 85.3 |
| 15 | " | " | B-1 (1.2) | " | " | 95.5 | 94.7 | 95.2 |
| 16 | " | " | B-13(1.2) | " | " | 95.2 | 94.8 | 94.9 |

TABLE 21-continued

| Run No. | Enzyme (U) | Alcohol | Fatty acid (moles based on alcohol) | Reaction system | Time (hrs) | Synthesis ratio (%) 1st | 2nd | 3rd |
|---|---|---|---|---|---|---|---|---|
| 17 | " | " | B-6 (1.2) | " | 24 | 87.8 | 89.3 | 87.9 |
| 18 | " | A-8 | B-8 (1.2) | " | " | 65.4 | 66.5 | 65.0 |
| 19 | " | " | B-3 (1.2) | " | " | 97.7 | 97.2 | 97.4 |
| 20 | " | " | B-1 (1.2) | " | 5 | 94.5 | 94.5 | 94.7 |
| 21 | " | " | B-13(1.2) | " | " | 89.7 | 88.9 | 90.0 |
| 22 | " | " | B-6 (1.2) | " | 24 | 94.3 | 93.8 | 94.2 |
| 23 | " | A-7 | B-3 (1.2) | " | 72 | 78.3 | 77.8 | — |
| 24 | " | " | B-1 (1.2) | " | " | 97.1 | 93.7 | — |
| 25 | " | " | B-13(1.2) | " | " | 95.4 | 93.9 | — |
| 26 | 2000 | A-1 | B-1 (3) | S-3 | 18 | 96.7 | 96.0 | 97.2 |
| 27 | " | " | " | S-4 | " | 96.8 | 95.9 | 96.0 |
| 28 | " | " | " | S-5 | " | 96.5 | 95.8 | 96.2 |
| 29 | " | " | " | S-6 | " | 96.0 | 95.8 | 96.2 |
| 30 | " | " | " | S-1 | " | 96.4 | 96.3 | 96.8 |

EXAMPLE 36

Celite No. 545 (40 g/ obtained from Johns Manville Sales Co.) was activated by heating in an electric oven at 500° C. for 2 hours and, then, immersed in a 2% acetone solution of aminopropyltriethoxysilane at 50° C. for 20 hours. After immersion, the Celite was washed with 400 ml of acetone and filtered to give silanated Celite.

Said silanated Celite (20 g) was immersed in a 1% aqueous solution of glutaraldehyde and, after overnight reaction at 4° C., washed well with 0.1 M phosphate buffer (pH 7.0), followed by filtration, which gave aldehydo-Celite.

To 1 g of said aldehydo-Celite were added 1,500 U of the enzyme and 2 ml of 0.1 M phosphate buffer, and immobilization was effected at 4° C. overnight, followed by filtration, which gave a glutaraldehydo-Celite-immobilized enzyme.

Separately, 1,500 U of the enzyme, 5 ml of 0.1 M phosphate buffer (pH 7.0) and 50 mg of a carbodiimide reagent [1-cyclohexyl-3-(morpholinoethyl)carbodiimide metho-p-toluenesulfonate] were added to 1 g of the above silanated Celite. Washing with water and filtration after overnight reaction at 4° C. gave a carbodiimido-Celite-immobilized enzyme.

Furthermore, a porous glass (CPG00500, average micropore size 257.7 Å, particle size 120–200 mesh, product of Electronucleonics) was used in lieu of Celite in the above procedures, which were performed in the same manner to give a glutaraldehydo-glass-immobilized enzyme and a carbodiimido-glass-immobilized enzyme.

The enzyme used was lipase MY.

To each of the immobilized enzyme preparations prepared in the above, there were added 100 mg of cholesterol, 220 mg of oleic acid and 2 ml of isooctane and 8 ml of 0.05 M phosphate buffer, and the reaction was carried out for 18 hours. After reaction, the reaction mixture was filtered, the immobilized enzyme recovered as a cake was returned to the reaction vessel together with the filter paper, and the reaction was repeated again in the above reaction system. This reaction procedure was repeated three times in all. The synthesis ratio obtained in the third reaction is shown below in Table 22.

TABLE 22

| Run No. | Enzyme used | Synthesis ratio in 3rd reaction (%) |
|---|---|---|
| 1 | Glutaraldehydo-Celite-immobilized enzyme | 93.5 |
| 2 | Carbodiimido-Celite-immobilized enzyme | 94.8 |
| 3 | Glutaraldehydo-glass-immobilized enzyme | 95.6 |
| 4 | Carbodiimido-glass-immobilized enzyme | 97.4 |

EXAMPLE 37

Immobilized enzyme preparations were obtained by following the procedure of Example 36 but using lipase T-01 in lieu of lipase MY.

Using the four immobilized enzyme preparations, the reaction was carried out in the same reaction system for 48 hours. As a result, synthesis ratio of 92.4%, 88.9%, 94.5% and 92.4% were obtained, respectively.

EXAMPLE 38

To 75 g of wet Cellulofine GC-700-m (product of Chisso Corp.) as obtained after washing with water and filtration, there were added 21.6 ml of 1 N aqueous sodium hydroxide and 12 ml of epichlorohydrin. The mixture was gently shaken at 30° C. for 4 hours to thereby effect epoxidization of hydrophilic hydroxyl groups exsisting on the micropore surface. The epoxidized Cellulofine was washed with 500 ml of distilled water, reacted with 6.7 ml of ethylenediamine and 1.05 ml of 1 N aqueous sodium hydroxide at 60° C. for 2.5 hours, then washed with water and collected by filtration. To 1 g of the ethylenediamine-coupled Cellulofine collected by suction filtration were added 10 ml of 0.1 M phosphate buffer (pH 7.0) and 1 ml of 25% glutaraldehyde solution, and the mixture was shaken overnight at room temperature, washed with phosphate buffer and filtered to give an aldehydo-Cellulofine.

The aldehydo-Cellulofine and 1,500 U of lipase MY were reacted overnight in phosphate buffer, giving a Cellulofine-immobilized lipase preparation.

A substrate solution composed of 100 mg of cholesterol, 220 mg of oleic acid and 2 ml of isooctane and 8 ml of phosphate buffer were added to the above immobilized enzyme preparation and the reaction was performed for 18 hours. After reaction, the reaction mixture was filtered, and the same substrate solution as above was added to the immobilized enzyme preparation recovered and the reaction was carried out again.

The above procedure was repeated three times in all. The synthesis ratio in the third reaction was 94.0%.

EXAMPLE 39

Dowex MWA-1 (1 g) was washed with distilled water and 1/15 M McIlvaine buffer (pH 5.0). Thereto was added 0.2 ml (1,500 U) of an aqueous lipase MY solution. The mixture was shaken overnight at 8° C. to thereby cause adsorption, followed by addition of 1 ml of McIlvaine buffer and 80 μl of 25% glutaraldehyde solution. The whole mixture was shaken at 8° C. for 10 minutes to effect coupling with the ion exchange resin. Finally, 0.2 ml of 20% sodium bisulfite was added and the resulting mixture was shaken at 80° C. for 10 minutes to thereby remove the excess glutaraldehyde. After washing with water, there was obtained an immobilized enzyme preparation.

The above immobilized enzyme preparation was added to a substrate solution composed of 100 mg of cholesterol, 220 mg of oleic acid and 15 ml of isooctane, and the reaction was carried out for 18 hours. After reaction, the reaction mixture was filtered and the reaction was carried out again in the same reaction system as in the first reaction using the immobilized enzyme thus recovered. The reaction was repeated three times in all.

As a result, the synthesis ratio in the third reaction was 96.5%.

EXAMPLE 40

One gram of Octyl-Sepharose CL-4B (product of Pharmacia Fine Chemicals) having increased hydrophobicity as a result of modification of agarose with hydrophobic octyl groups was washed well with 0.1 M phospahte buffer (pH 7.0) and filtered. To this was added a solution of 3,000 U of lipase MY in 5 ml of 0.05 M phosphate buffer, and was shaken gently at 0° C. for 1 hour to thereby effect adsorption of the enzyme onto Octyl-Sepharose. After 1 hour, the resin was washed with 1 ml of phosphate buffer, collected by filtration and submitted to the reaction.

The reaction was carried out in the same manner as in Example 39 except that the reaction time was 16 hours.

After 4 repetitions of the above reaction, the synthesis ratio in the fourth reaction was 94.8%.

EXAMPLE 41

To 1 g of Celite were added 2,000 U of lipase MY or 1,000 U of cholesterol esterase T-18 and 5 ml of phosphate buffer (pH 7.0), and the mixture was shaken at room temperature for 1 hour to cause adsorption. After 1 hour, the Celite was filtered off, washed with 1 ml of phosphate buffer, returned to the reaction vessel together with the filter paper and used as an immobilized enzyme.

The reaction was repeated five times in the same manner as in Example 39 except that the reaction time was 18 hours. The synthesis ratio in the fifth reaction was 94.1% when the immobilized lipase MY was used and 94.5% when the immobilized cholesterol esterase was used.

EXAMPLE 42

In this example, the relationship between the synthesis ratio of the sterol ester and the raw material quantity ratio (substrate ratio), fatty acid ester to sterol, was studied.

Thus, 100 mg of cholesterol (hereinafter abbreviated as "cho") and a specified amount of methyl oleate (hereinafter, "MO") were used and a solution of 1,000 U (33.3 mg) of lipase MY in 8 ml of 0.05 M phosphate buffer (pH 7.0) (hereinafter, "PB") was added to the reaction system. The above substrates were dissolved in 3.0 ml of isooctane, so that the reaction system was a water-organic solvent two-phase system. The reaction vessel used was a cylindrical glass bottle, 3 cm in inside diameter and 5 cm in height, with a screw cap. In the examples that follow, the same shall apply unless otherwise specifically stated.

The synthesis ratio of the cholesteryl oleate (hereinafter, "CO") as obtained by 2 hours of reaction is given in Table 23 for each run. The ratio was calculated by the following equation (2):

$$\text{Synthesis ratio (\%)} = (CO \text{ peak area}) \times 100 / (CO \text{ peak area} + cho \text{ peak area}) \quad (2)$$

In the examples that follow, unless otherwise stated, synthesis ratio calculation was performed using the above equation (2).

TABLE 23

| Run No. | Amount of MO (moles per mole of cho) | Synthesis ratio (%) |
|---------|--------------------------------------|---------------------|
| 1 | 1.0 | 41.9 |
| 2 | 1.5 | 45.3 |
| 3 | 2.0 | 63.4 |
| 4 | 3.0 | 69.1 |
| 5 | 4.0 | 71.6 |
| 6 | 5.0 | 74.0 |
| 7 | 6.0 | 98.3 |

The data indicate a tendency toward increase in the synthesis ratio with an increasing MO/cho mole ratio.

EXAMPLE 43

The reaction was conducted in the same manner as in Example 42 except that using 100 mg of cho, a specified amount of MO shown in Table 24, 2 ml of isooctane, 8 ml of PB and 500 U of lipase MY and that the reaction time was 6 hours. The results obtained are shown in Table 24. Since cho was used in large excess, the synthesis ratio was calculated by the following equation (3):

$$\text{Synthesis ratio (\%)} = (CO \text{ peak area}) \times 100 / (CO \text{ peak area} + MO \text{ peak area} + \text{oleic acid peak area}) \quad (3)$$

TABLE 24

| Run No. | Amount of MO (moles per mole of cho) | Synthesis ratio (%) |
|---------|--------------------------------------|---------------------|
| 1 | 1.0 | 81.2 |
| 2 | 0.8 | 81.1 |
| 3 | 0.7 | 82.2 |
| 4 | 0.6 | 87.0 |
| 5 | 0.5 | 89.3 |
| 6 | 0.4 | 90.3 |
| 7 | 0.3 | 90.2 |
| 8 | 0.2 | 94.4 |
| 9 | 0.1 | 97.3 |

Unlike Table 23, Table 24 shows that, when cho is used in excess, the synthesis ratio increases as the amount of MO, hence the mole ratio, decreases. Considering the results in this example and in Example 42, it may be concluded that either of the substrates may be in excess and that a greater difference in the number of moles gives a higher synthesis ratio.

EXAMPLE 44

In this example, the synthesis ratio of the desired ester was examined in an aqueous medium system and in a water-containing organic solvent system.

Thus, the reaction vessel was charged with 100 mg of cho, 230 mg of MO and 1,000 U of lipase MY, followed by addition of PB and/or isooctane in respective amounts given in Table 25. Then, the reaction was carried out for 4 hours. The results obtained are shown in Table 25.

TABLE 25

| Run No. | Isooctane (ml) | PB (ml) | Synthesis ratio (%) |
|---|---|---|---|
| 1 | 0 | 10 | 59.5 |
| 2 | 1 | 9 | 96.8 |
| 3 | 2 | 8 | 97.3 |
| 4 | 3 | 7 | 93.4 |
| 5 | 4 | 6 | 78.2 |
| 6 | 5 | 5 | 55.4 |
| 7 | 6 | 4 | 64.3 |
| 8 | 7 | 3 | 25.3 |
| 9 | 8 | 2 | 51.2 |
| 10 | 9 | 1 | 85.4 |
| 11 | 10 | 0 | 21.1 |

Table 25 indicates that when the total reaction mixture volume is 10 ml, the synthesis ratio is maximal at an isooctane/PB ratio of about 2 ml/8 ml. In the PB-free system, the desired reaction supposedly takes place as a result of expression of the enzyme activity owing to water contained in water-saturated isooctane, substrates and enzyme. The synthesis ratio is low in that case presumably because the enzyme remains as a solid in the reaction mixture to form flocs, which make it difficult for the enzyme supposedly functioning at the water-hydrophobic layer interface to have a sufficient contact area and which results in such small amount of water available for the hydrolysis of the raw fatty acid ester as compared with other reaction conditions that said hydrolysis reaction is rendered rate-determining.

EXAMPLE 45

The reaction was carried out using isooctane and PB in amounts shown in Table 26 and a 500-ml Sakaguchi flask as the reaction vessel. The reaction conditions were the same as in Example 44 except that the Sakaguchi flask was shaken on a shaker (Iwashiya Bio-Science Co., Ltd.) at a stroke of 6 cm and a frequency of 120 cpm. The results obtained are shown in Table 26.

TABLE 26

| Run No. | Total volume (ml) | Isooctane/PB volume ratio | Synthesis ratio (%) |
|---|---|---|---|
| 1 | 30 | 4/1 | 54.4 |
| 2 | " | 3/2 | 91.4 |
| 3 | " | ⅔ | 95.1 |
| 4 | " | ¼ | 96.2 |
| 5 | 60 | 4/1 | 68.9 |
| 6 | " | 3/2 | 88.5 |
| 7 | " | ⅔ | 93.4 |
| 8 | " | ¼ | 95.7 |
| 9 | 100 | 4/1 | 64.7 |
| 10 | " | 3/2 | 80.1 |
| 11 | " | ⅔ | 88.3 |
| 12 | " | ¼ | 94.1 |
| 13 | 200 | 4/1 | 40.7 |
| 14 | " | 3/2 | 56.1 |
| 15 | " | ⅔ | 82.6 |
| 16 | " | ¼ | 89.7 |
| 17 | 300 | 4/1 | 16.5 |
| 18 | " | 3/2 | 35.7 |
| 19 | " | ⅔ | 76.2 |
| 20 | " | ¼ | 78.1 |

Table 26 shows that this system exhibits a tendency toward decrease in the synthesis ratio as the total volume of the reaction mixture increases and that the ratio increases with the increase of the proportion of PB in the reaction system irrespective of the reaction mixture volume.

EXAMPLE 46

In this example, the reaction was performed in an aqueous medium system (in which PB alone was used without any organic solvent) using 1,000 U of lipase MY and cho and MO as substrates in amounts given in Table 27 (the mole ratio cho/MO being constantly ½) to give the desired CO. The results thus obtained are shown in Table 27.

To the systems in which PB was used in an amount of 0.5 ml, one glass bead, 12 mm in diameter, was placed in the reaction vessel for improving the state of mixing.

In Table 27, there are also shown synthesis amounts of CO calculated using an area-to-weight conversion table constructed using standard cholesteryl oleate solutions.

TABLE 27

| Run No. | cho (mg) | MO (mg) | PB (ml) | Time (hrs) | Synthesis ratio (%) | Amount of CO (mg) |
|---|---|---|---|---|---|---|
| 1 | 100 | 153 | 0.5 | 23 | 94.8 | 141 |
| 2 | " | " | 8.0 | " | 70.3 | 97 |
| 3 | " | " | 20.0 | " | 88.8 | 126 |
| 4 | 200 | 307 | 0.5 | " | 75.4 | 210 |
| 5 | 800 | 1227 | 0.5 | 48 | 30.4 | 392 |
| 6 | " | " | 8.0 | " | 88.2 | 996 |
| 7 | " | " | 20.0 | " | 75.1 | 836 |
| 8 | 1000 | 1534 | 8.0 | " | 85.8 | 1200 |
| 9 | " | " | 20.0 | " | 83.3 | 1157 |
| 10 | 1200 | 1840 | 8.0 | " | 84.5 | 1412 |
| 11 | " | " | 20.0 | " | 80.7 | 1344 |
| 12 | 1400 | 2147 | 8.0 | " | 80.8 | 1571 |
| 13 | " | " | 20.0 | " | 79.8 | 1554 |
| 14 | 1600 | 2454 | 8.0 | 160 | 84.4 | 1880 |
| 15 | " | " | 20.0 | " | 93.6 | 2197 |
| 16 | 1800 | 2760 | 8.0 | " | 86.9 | 2196 |
| 17 | " | " | 20.0 | " | 91.7 | 2376 |
| 18 | 2000 | 3067 | 8.0 | " | 84.4 | 2350 |
| 19 | " | " | 20.0 | " | 83.7 | 2330 |

EXAMPLE 47

In this example, changes in the synthesis ratio depending on the kind of solvent were investigated by conducting the reaction for 29 hours using a system composed of 100 mg of cho, 230 mg of MO, 500 U of lipase MY and organic solvent/PB=2 ml/8 ml. The organic solvents used and the results obtained are shown in Table 28.

TABLE 28

| Run No. | Organic solvent used | Synthesis ratio (%) |
|---|---|---|
| 1 | Isooctane | 99.0 |
| 2 | Cyclohexane | 99.5 |

TABLE 28-continued

| Run No. | Organic solvent used | Synthesis ratio (%) |
| --- | --- | --- |
| 3 | n-Hexadecane | 69.5 |

EXAMPLE 48

In this example, changes in the synthesis ratio with time were studied by conducting the reaction using a system composed of 100 mg of cho, 230 mg of MO, 1,000 U of lipase MY and isooctane/PB=5 ml/5 ml to 1 ml/9 ml. The results obtained are shown in Table 29.

TABLE 29(1)

| Run No. | Time (hr) | Isooctane/PB (ml/ml) | Synthesis ratio (%) |
| --- | --- | --- | --- |
| 1 | 0.5 | 5/5 | 1.0 |
| 2 | " | 4/6 | 2.6 |
| 3 | " | 3/7 | 4.6 |
| 4 | " | 2/8 | 17.0 |
| 5 | " | 1/9 | 47.5 |
| 6 | 1.0 | 5/5 | 4.2 |
| 7 | " | 4/6 | 8.5 |
| 8 | " | 3/7 | 12.1 |
| 9 | " | 2/8 | 33.1 |
| 10 | " | 1/9 | 64.4 |
| 11 | 2.0 | 5/5 | 15.9 |
| 12 | " | 4/6 | 32.5 |
| 13 | " | 3/7 | 57.5 |
| 14 | " | 2/8 | 65.8 |
| 15 | " | 1/9 | 96.6 |
| 16 | 3.0 | 5/5 | 33.1 |
| 17 | " | 4/6 | 47.0 |
| 18 | " | 3/7 | 66.7 |
| 19 | " | 2/8 | 88.6 |
| 20 | " | 1/9 | 95.6 |

TABLE 29(2)

| Run No. | Time (hr) | Isooctane/PB (ml/ml) | Synthesis ratio (%) |
| --- | --- | --- | --- |
| 21 | 4.0 | 5/5 | 54.8 |
| 22 | " | 4/6 | 77.8 |
| 23 | " | 3/7 | 93.3 |
| 24 | " | 2/8 | 97.2 |
| 25 | " | 1/9 | 96.8 |
| 26 | 5.0 | 5/5 | 90.5 |
| 27 | " | 4/6 | 89.6 |
| 28 | " | 3/7 | 94.1 |
| 29 | " | 2/8 | 97.5 |
| 30 | " | 1/9 | 96.6 |
| 31 | 6.0 | 5/5 | 92.6 |
| 32 | " | 4/6 | 95.2 |
| 33 | " | 3/7 | 95.6 |
| 34 | " | 2/8 | 97.2 |
| 35 | " | 1/9 | 96.2 |
| 36 | 16.0 | 5/5 | 94.6 |
| 37 | " | 4/6 | 96.2 |
| 38 | " | 3/7 | 97.3 |
| 39 | " | 2/8 | 97.3 |
| 40 | " | 1/9 | 96.3 |

The data in Table 29 indicate that, even in isooctane/PB systems in which the reaction velocity is slow, a synthesis ratio of 95% can be achieved by prolonging the reaction time.

EXAMPLE 49

The reaction was carried out using 100 mg of cho, a specified amount (given in Table 30) of a fatty acid methyl ester, an enzyme and isooctane/0.05 M phosphate buffer (pH 7.0) (shown "ioc/PB" in the table). The reaction time and results obtained are also shown in Table 30. The synthesis ratio was calculated by the following equation (4):

$$\text{Synthesis ratio (\%)} = \text{(sterol ester peak area)} \times 100/\text{(sterol ester peak area + cho peak area)} \quad (4)$$

The symbols used in Table 30 are either as defined above or as follows:

Fatty Acid Esters

C-1: Methyl propionate
C-2: Methyl caprate
C-3: Methyl stearate
C-4: Methyl behenate
C-5: Methyl oleate
C-6: Lanolin fatty acid methyl esters (product of Yoshikawa Oil and Fat Co., Ltd.)
C-7: Methyl isostearate (prepared from Emery's isostearic acid)
C-8: Methyl linoleate
C-9: Methyl 12-hydroxystearate
C-10: Dimethyl succinate

TABLE 30

| Run No. | Enzyme (U) | Fatty acid ester (mole ratio to cho) | | ioc/PB (ml/ml) | Time (hrs) | Synthesis ratio (%) |
| --- | --- | --- | --- | --- | --- | --- |
| 1 | E-1 (1000) | C-1 | (1.2) | 2/8 | 120 | 43.3 |
| 2 | " | C-2 | (1.2) | " | 24 | 94.7 |
| 3 | " | C-3 | (1.2) | " | 24 | 80.4 |
| 4 | " | C-4 | (1.2) | " | 24 | 69.4 |
| 5 | " | C-5 | (1.2) | " | 24 | 97.3 |
| 6 | " | C-6 | (1.2) | " | 48 | 82.2 |
| 7 | " | C-7 | (1.2) | " | 24 | 74.6 |
| 8 | " | C-8 | (1.2) | " | 24 | 92.7 |
| 9 | E-2 (1000) | C-2 | (1.2) | " | 120 | 78.2 |
| 10 | " | C-3 | (1.2) | " | 48 | 92.2 |
| 11 | " | C-4 | (1.2) | " | 48 | 74.2 |
| 12 | " | C-5 | (2.0) | ⅜ | 21 | 84.5 |
| 13 | " | C-7 | (1.2) | 2/8 | 48 | 85.5 |
| 14 | " | C-8 | (1.2) | " | 48 | 92.9 |
| 15 | " | C-9 | (1.2) | " | 120 | 63.0 |
| 16 | E-3 (1000) | C-3 | (1.2) | " | 48 | 62.4 |
| 17 | " | C-4 | (1.2) | " | 96 | 71.3 |
| 18 | " | C-5 | (2.0) | ⅜ | 45 | 89.9 |
| 19 | " | C-10 | (1.2) | 2/8 | 120 | 65.3 |
| 20 | E-7 (10000) | C-3 | (1.2) | " | 96 | 75.9 |
| 21 | " | C-5 | (1.2) | " | 96 | 88.3 |
| 22 | " | C-6 | (1.2) | " | 72 | 50.5 |
| 23 | " | C-8 | (1.2) | " | 120 | 69.7 |
| 24 | E-5 (350) | C-5 | (2.0) | ⅜ | 2 | 96.8 |
| 25 | E-6 (500) | C-5 | (2.0) | 2/8 | 3 | 97.4 |

EXAMPLE 50

The reaction was carried out using a sterol component given in Table 31 (in an amount of 100 mg), MO (mole ratio to cho=1.2), 1,000 U of lipase MY and isooctane/PB=2 ml/8 ml. The reaction time and the results obtained are also shown in Table 31. The synthesis ratio was calculated by the following equation (5):

$$\text{Synthesis ratio (\%)} = \text{(sterol ester peak area)} \times 100/\text{(sterol ester peak area + sterol peak area)} \quad (5)$$

TABLE 31

| Run No. | Sterol component | Reaction time (hrs) | Synthesis ratio (%) |
| --- | --- | --- | --- |
| 1 | Cholesterol | 24 | 92.2 |
| 2 | β-Sitosterol | 24 | 89.7 |
| 3 | Stigmasterol | 24 | 95.4 |
| 4 | Ergosterol | 24 | 94.0 |

TABLE 31-continued

| Run No. | Sterol component | Reaction time (hrs) | Synthesis ratio (%) |
|---|---|---|---|
| 5 | Dihydrocholesterol | 72 | 93.1 |

EXAMPLE 51

The reaction was carried out for 70 hours using 100 mg of cho and 200 mg of a starting fatty acid ester shown in Table 32 as substrates, together with 1,000 U of lipase MY, in a solvent of isooctane/PB=5 ml/10 ml. The synthesis ratio calculated in the same manner as in Example 42 are shown in Table 32.

TABLE 32

| Run No. | Starting fatty acid ester | Synthesis ratio (%) |
|---|---|---|
| 1 | Methyl palmitate | 99.2 |
| 2 | Ethyl palmitate | 98.3 |
| 3 | Isopropyl palmitate | 98.7 |
| 4 | Isobutyl palmitate | 97.4 |
| 5 | Methyl stearate | 97.6 |

EXAMPLE 52

The reaction was conducted for 1.5 hours using, as substrates, 100 mg of cho and a quantity of olive oil as specified in Table 33, together with 500 U of lipase MY, in isooctane/PB=2 ml/8 ml. In all the runs, olive oil was completely hydrolyzed in 1.5 hours. The results obtained are shown in Table 33. The synthesis ratio for run Nos. 1 and 2 were calculated according to the equation (2) mentioned above and those for run Nos. 3–5 were calculated by the following equation (6):

$$\text{Synthesis ratio (\%)} = (\text{CO peak area}) \times 100/(\text{CO peak area} + \text{fatty acid peak area}) \quad (6)$$

TABLE 33

| Run No. | Olive oil (mg) | Synthesis ratio (%) |
|---|---|---|
| 1 | 229 | 96.6 |
| 2 | 114.5 | 94.5 |
| 3 | 76.3 | 96.3 |
| 4 | 57.2 | 97.1 |
| 5 | 45.8 | 97.5 |

EXAMPLE 53

The reaction was conducted using, as substrates, 100 mg of cho and specified amounts of an oil or fat given in Table 34, together with 1,000 U of lipase MY. The reaction system, reaction time and the results obtained are shown in Table 34. The synthesis ratio was calculated according to the equation (2).

TABLE 34

| Run No. | Oil or fat (mg) | ioc/PB (ml/ml) | Time (hrs) | Synthesis ratio (%) |
|---|---|---|---|---|
| 1 | Caster oil (240) | 2/8 | 96 | 61.4 |
| 2 | Caster oil (240) | 10/15 | 96 | 73.6 |
| 3 | Hydrogenated caster oil (235) | 2/8 | 45 | 62.3 |
| 4 | Hydrogenated caster oil (235) | 10/15 | 45 | 59.6 |

EXAMPLE 54

The reaction was effected by stirring for 3 hours a mixture composed of 100 mg of cho, 153 mg of MO, 2 ml of isooctane, 8 ml of PB and 1,000 U of lipase MY. Then, the upper layer was sampled and assayed for the synthesis ratio of CO.

Thereafter, the mixture was allowed to stand, the upper isooctane layer was removed while leaving that interface portion with the aqueous layer, followed by further addition of 16 ml of isooctane. After stirring and standing, 15 ml of the isooctane layer was removed to thereby wash away the unreacted substrates and the reaction product remaining in the interface portion. After repeating the above procedure twice in all, 100 mg of cho, 153 mg of MO and 1 ml of isooctane were again added to the enzyme-containing aqueous layer and the reaction was performed for 3 hours.

The invention was practiced by repeating 7 times in all the above procedure comprising removing the upper substrate- and reaction product-containing isooctane layer after reaction while leaving the aqueous lipase-containing layer and the interface layer, and then adding new portions of substrates and isooctane.

The results thus obtained are shown in Table 35. During the period from assaying the synthesis ratio to addition of new substrate portions, the reaction mixture was maintained in a state in which the enzyme and substrates were in contact with one another.

TABLE 35

| Repeated reaction run No. | Synthesis ratio (%) |
|---|---|
| 1 | 91.0 |
| 2 | 91.4 |
| 3 | 90.4 |
| 4 | 91.1 |
| 5 | 92.3 |
| 6 | 90.5 |
| 7 | 89.6 |

The data in Table 35 indicate that repetition of the above synthesis reaction does not lead to any loss in enzyme activity at all.

EXAMPLE 55

The procedure of Example 21 was repeated using 230 mg of methyl α-hydroxypalmitate in lieu of α-hydroxypalmitic acid.

The synthesis ratio in the first reaction was 72.5% and that in the second reaction was 70.4%.

EXAMPLE 56

The continuous reaction apparatus shown by the flowchart in FIG. 6 was used, the column portion (G2) thereof was filled with 500 ml of a 108 U/ml lipase MY solution in PB, and a substrate solution composed of cho/MO/isooctane=1,200 mg/1,840 mg/600 ml was introduced into the aqueous enzyme solution layer portion (G2) in the form of oily droplets at a rate of 8.52 ml/min through the column bottom nozzle (N1) by means of the pump (P1). The reaction product-containing isooctane layer as separated in the portion (G1) of the glass column was withdrawn continuously at a rate of 0.127 ml/min into the reaction mixture tank (T4). The isooctane solution overflowing from the receptacle (T1) was led to the mixing vessel (T2), where said solution was mixed with a new substrate solution having the same composition as above as fed at a rate of 0.127 ml/min from the raw material tank (T3) by means of the pump (P3). The resulting substrate solution was fed again to the (G2) portion of the glass column at a rate of 8.52 ml/min by means of the pump (P1) through the nozzle (N1).

In this manner, the substrate solution was recycled into the aqueous enzyme solution repeatedly while sampling the reaction mixture at 3-hour intervals using the autosampler (A). The results of assay of the samples for ester synthesis ratio are shown in FIG. 9 obtained in the same manner as FIG. 7.

Until about 48 hours after start of the reaction, the isooctane layer in the upper part (G1) of the column was in an emulsified state. However, phase separation began as the reaction proceeded and was complete at about 64 hours.

Figure 9:
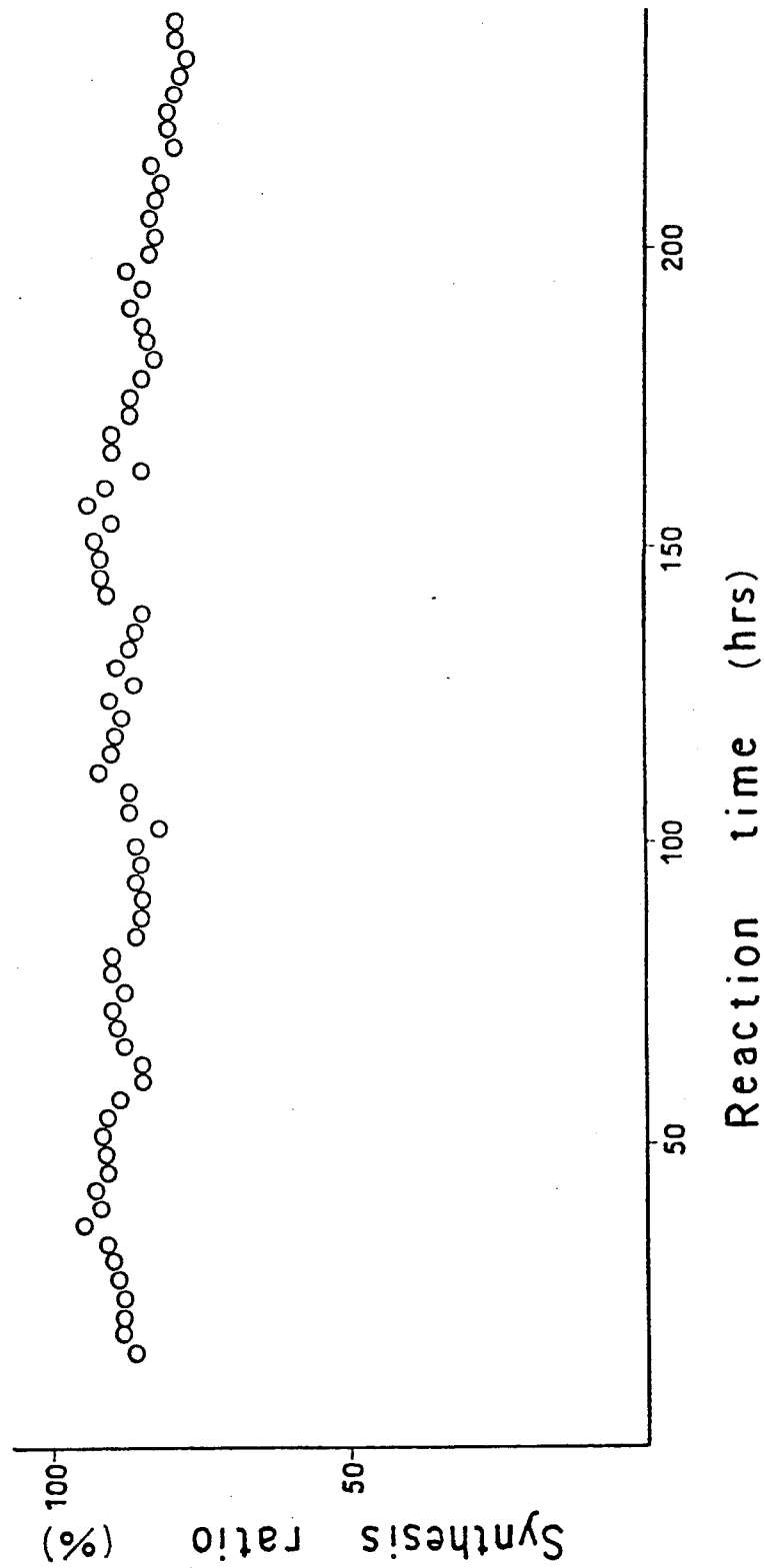
FIG. 9 is a graph of the results obtained in Example 56, showing the ester synthesis ratio versus reaction time.

FIG. 9 shows that when the above procedure is followed, the desired ester can be continuously synthesized using the enzyme repeatedly and that the synthesis ratio can be maintained at a level not less than 80% without replacement or supplementation of the enzyme for 240 hours or longer.

EXAMPLE 57

A vessel was divided into two compartments with Duraguard 2500. The lower compartment (8 cm³ in capacity) below said membrane was filled with 8 cm³ of an aqueous 595 U/ml solution of lipase MY. A communication tube connected thereto was also filled with the same aqueous enzyme solution, so that the liquid level in said tube was 30 cm higher than the membrane level.

The upper compartment of the above vessel was charged with a substrate solution composed of 100 mg of cho, 153 mg of MO and 10 ml of isooctane. The reaction was carried out for 48 hours while shaking the whole vessel on a shaker reciprocating at a stroke of 6 cm and a frequency of 120 cpm. As a result, a synthesis ratio of 87.2% was obtained. The reaction system was not emulsified. No penetration of water into the substrate phase was observed.

EXAMPLE 58

Duraguard 2500 was immersed in methanol and in water to thereby render the membrane hydrophilic as a result of substitution of the micropore contents with water. This hydrophilic membrane was used in place of Duraguard 2500 used in Example 57. The upper and lower compartments relative to said membrane were charged with the same substrate solution and aqueous enzyme solution, respectively. In this example, the communication tube liquid level was the same as the membrane level, however.

The reaction was conducted in the same manner as in Example 57 and, when the synthesis ratio arrived at 90% or higher, substrate solution replacement was made. The reaction was repeated in this way 10 times in all. The synthesis ratio and the amounts of CO were determined for each run.

Figure 10:
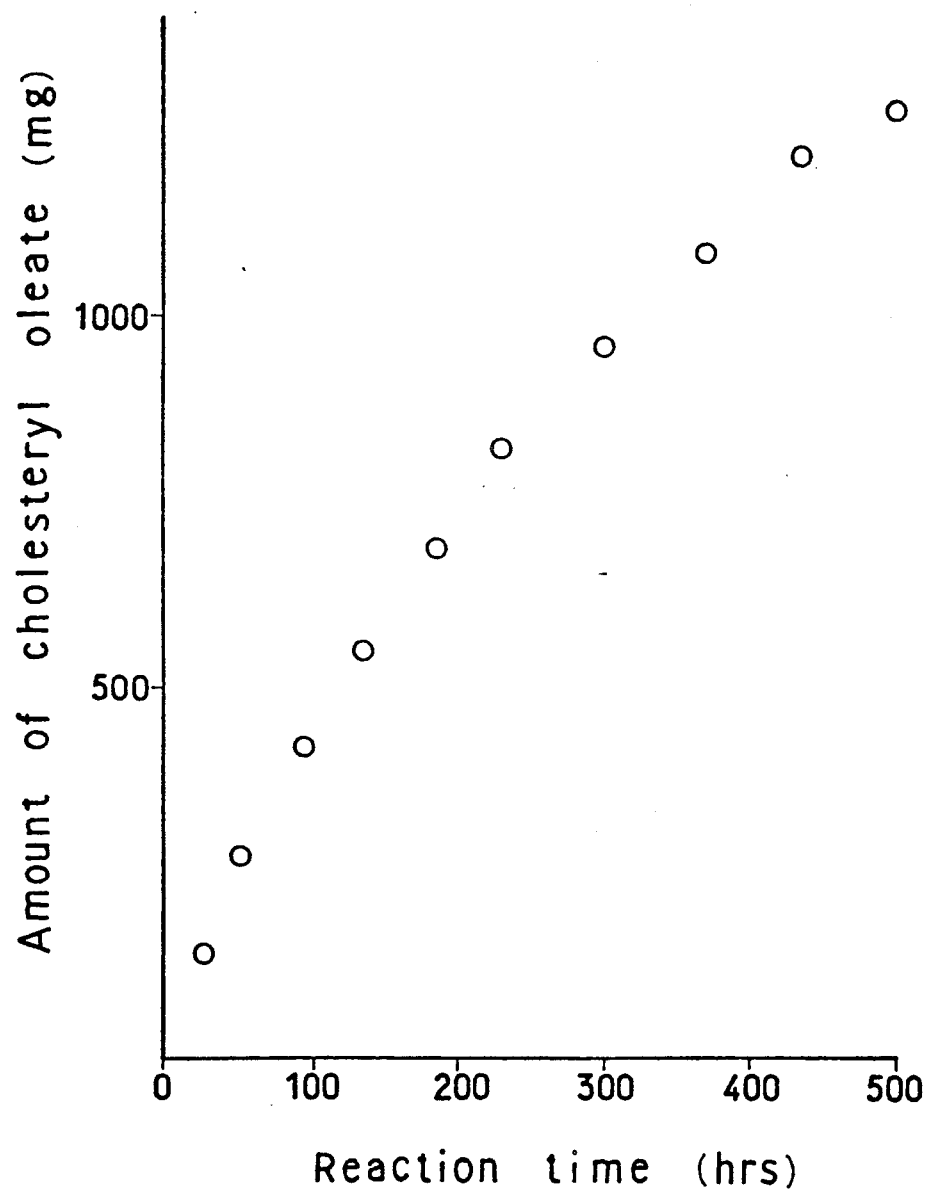
FIG. 10 is a graph of the results obtained from Example 58, showing the amount of cholesteryl oleate versus reaction time.

The results obtained are shown in FIG. 10. In the figure, the abscissa indicates the reaction time (hrs) and the ordinate the amount of CO (mg).

FIG. 10 shows that when a hydrophilic membrane is used, the aqueous enzyme solution permeates the micropores of the membrane and comes into contact with the substrates above the membrane to catalyze the reaction, so that the reaction can be continued without need of supplementation or replacement of the enzyme for about 500 hours or longer and gives 1,280 mg of CO after 500 hours.

EXAMPLE 59

The procedure of Example 57 was followed using five kinds of membranes given in Table 36. The lower compartment had a volume of 8 cm³. The reaction was carried out in the same manner as in Example 57. The results thus obtained are also shown below in Table 36.

TABLE 36

| Run No. | 1 | 2 | 3 | 4 | 5 |
| --- | --- | --- | --- | --- | --- |
| Membrane material | Regenerated cellulose | Teflon | Nitro-cellulose | Nitro-cellulose | Hydrophilic membrane obtained in Example 58 |
| Average pore size (μm) | 0.45 | 0.5 | 0.45 | 3.0 | 0.1 |
| Level difference between communicating tube and membrane (cm) | 0 | 30 | 0 | 0 | 0 |
| Reaction time (hrs) | 48 | 48 | 48 | 48 | 48 |
| Synthesis ratio (%) | 90.4 | 85.6 | 90.3 | 92.6 | 93.2 |
| Emulsification | None | None | None | None | None |

Table 36 shows that the synthesis reaction proceeds smoothly with any of the membranes, without emulsification of the reaction system.

EXAMPLE 60

A glass column, 2 cm in inside diameter and 46 cm in length, was charged with 900,000 U (30 g) of the immobilized lipase MY as prepared in the same manner as in the procedure (2) of Example 31 to a height of about 36 cm. A substrate solution composed of 1,000 mg of cho, 1,534 mg of MO and 150 ml of isooctane was circulated through the above column at a rate of 6.3 ml/min. When the CO synthesis ratio reached about 80%, the substrate solution was replaced with a new one and the reaction was repeated.

Figure 11:
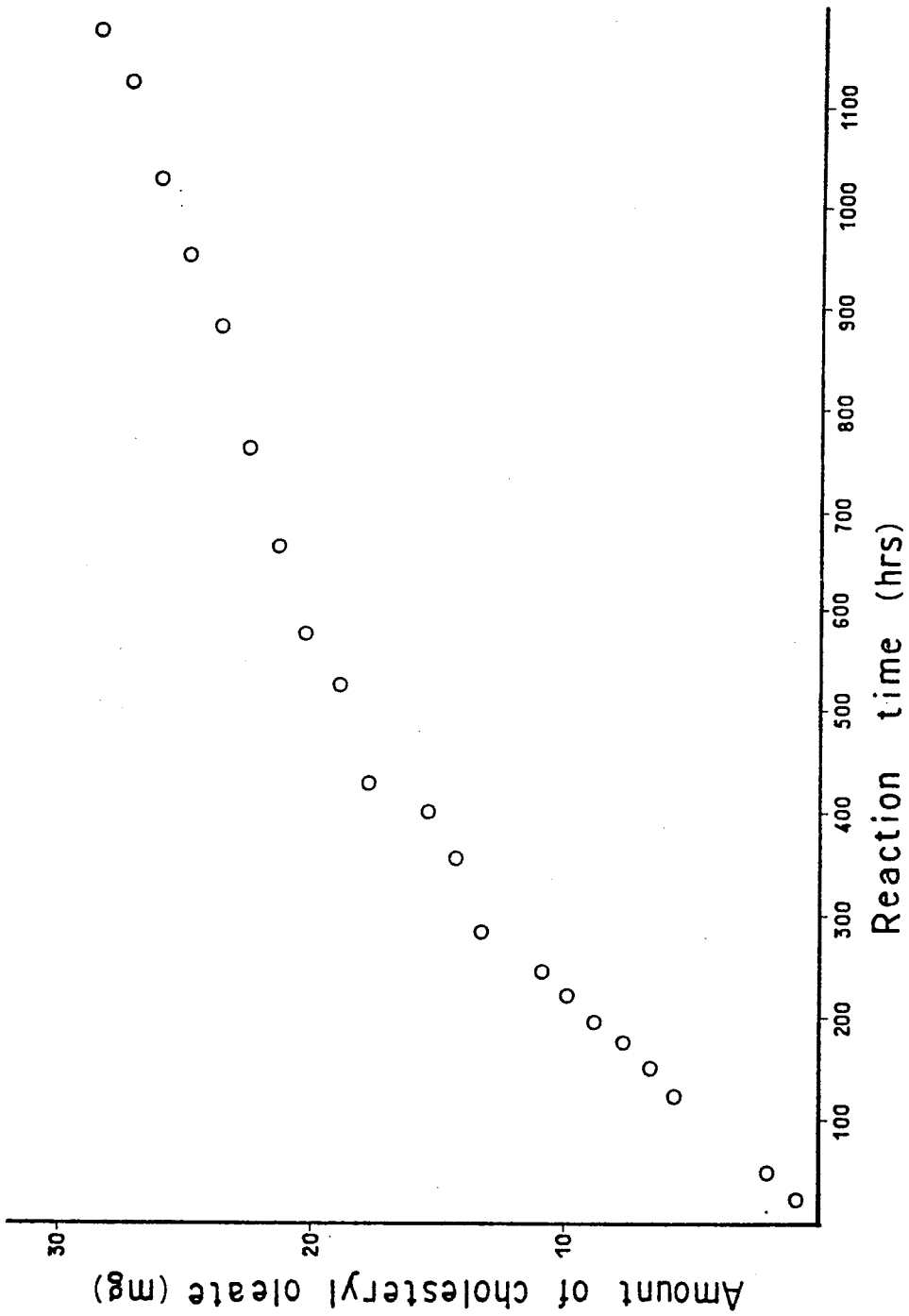
FIG. 11 is a graph of the results obtained from Example 60, plotted in the same manner as FIG. 10.

As in Example 46 (Table 27), the synthesis ratio obtained in each run was converted to the synthesis amount of CO and the relation between said amount and the reaction time was studied. The results obtained are shown in FIG. 11 in the same manner as FIG. 10.

EXAMPLE 61

To 2,000 U (19.0 mg) of the immobilized cholesterol esterase T-18 were added 100 mg of cho, 153 mg of MO and 15 ml of isooctane, and the reaction was carried out. The reaction mixture was filtered once a day except for holidays and, using the thus-recovered immobilized enzyme, the reaction was repeated for 79 days in the same reaction system as in the first reaction while replacing the substrate solution with a new one each time. The time course of the reaction on the 80th day is shown in Table 37.

TABLE 37

| Reaction time (hrs) | Synthesis ratio (%) |
|---|---|
| 1 | 29.4 |
| 3 | 72.1 |
| 5 | 81.9 |
| 18 | 84.6 |
| 23 | 91.7 |

EXAMPLE 62

To each immobilized enzyme preparation prepared in the same manner as in Example 36 were added 100 mg of cho, 230 mg of MO, 2 ml of isooctane and 8 ml of PB, and the reaction was carried out for 24 hours. Thereafter, the reaction mixture was filtered, the immobilized enzyme thus recovered as a cake was returned to the reaction vessel together with the filter paper, and the reaction was repeated in the same reaction system as above. This procedure was repeated three times in all. The synthesis ratio in the third reaction is shown below in Table 38 for each enzyme preparation.

TABLE 38

| Run No. | Enzyme preparation used | Synthesis ratio in 3rd reaction (%) |
|---|---|---|
| 1 | Glutaraldehydo-Celite-immobilized enzyme | 78.9 |
| 2 | Carbodiimido-Celite-immobilized enzyme | 54.6 |
| 3 | Glutaraldehydo-glass-immobilized enzyme | 70.6 |
| 4 | Carbodiimido-glass-immobilized enzyme | 65.4 |

EXAMPLE 63

To the immobilized enzyme preparation produced in the same manner as in Example 38 were added a substrate solution composed of 100 mg of cho, 230 mg of MO and 2 ml of isooctane and 8 ml of PB, and the reaction was conducted for 24 hours. After reaction, the reaction mixture was filtered, the same substrate solution as above was added to the immobilized enzyme preparation recovered, and the reaction was again carried out.

The above procedure was repeated three times. The synthesis ratio in the third reaction was 95.2%.

EXAMPLE 64

Using specified amounts of an enzyme, an alcohol component and a fatty acid or fatty acid ester component each given in Table 39, the reaction was carried out in isooctane/PB=3 ml/8 ml. The reaction time and the result obtained are shown in the same table.

The symbols used in Table 39 are either as defined above or as follows:

Fatty Acid Esters

C-11: Triolein (product of Tokyo Kasei Kogyo Co., Ltd.)
C-12: Tristearin (product of Tokyo Kasei Kogyo Co., Ltd.)
C-13: Trilaurin (product of Tokyo Kasei Kogyo Co., Ltd.)
C-14: Tributylin (product of Tokyo Kasei Kogyo Co., Ltd.)
C-15: Soybean oil
C-16: Tallow
C-17: Cotton seed oil
C-18: Olive oil

TABLE 39(1)

| Run No. | Enzyme (U) | Alcohol (mg) | Fatty acid or fatty acid ester (mg) | Time (hrs) | Synthesis ratio (%) |
|---|---|---|---|---|---|
| 1 | E-1 (1000) | A-7 (51.8) | B-1 (147) | 24 | 76.4 |
| 2 | " | A-8 (78.1) | " | 1 | 99.3 |
| 3 | " | A-9 (90.5) | " | 3 | 94.5 |
| 4 | " | A-10 (69.7) | " | 24 | 99.3 |
| 5 | " | A-7 (51.8) | C-5 (153) | 120 | 75.4 |
| 6 | " | A-8 (78.1) | C-2 (96.3) | 3 | 89.5 |
| 7 | " | " | C-3 (154) | 3 | 86.6 |
| 8 | " | " | C-5 (153) | 3 | 99.1 |
| 9 | " | A-9 (90.5) | C-2 (96.3) | 5 | 85.4 |
| 10 | " | " | C-5 (153) | 5 | 89.7 |
| 11 | " | A-10 (69.7) | C-3 (154) | 24 | 93.3 |
| 12 | " | " | C-5 (153) | 3 | 95.8 |
| 13 | " | A-1 (100) | C-11 (229) | 3 | 96.4 |
| 14 | " | " | C-12 (231) | 3 | 92.2 |
| 15 | " | " | C-13 (165) | 3 | 89.3 |

TABLE 39(2)

| Run No. | Enzyme (U) | Alcohol (mg) | Fatty acid or fatty acid ester (mg) | Time (hrs) | Synthesis ratio (%) |
|---|---|---|---|---|---|
| 16 | E-1 (1000) | A-1 (100) | C-14 (78.2) | 24 | 83.6 |
| 17 | " | " | C-15 (226) | 3 | 92.0 |
| 18 | " | " | C-16 (222) | 3 | 94.4 |
| 19 | " | " | C-17 (224) | 3 | 95.2 |
| 20 | E-4 (66.7) | " | B-1 (147) | 3 | 96.6 |
| 21 | E-6 (6.7) | " | C-5 (153) | 3 | 94.6 |
| 22 | E-4 (66.7) | " | " | 24 | 95.4 |
| 23 | E-6 (6.7) | " | C-18 (227) | 1 | 97.5 |
| 24 | E-4 (66.7) | " | " | 3 | 97.4 |
| 25 | E-6 (6.7) | " | B-12 (147) | 24 | 86.7 |
| 26 | E-4 (66.7) | " | " | 5 | 90.8 |
| 27 | E-1 (1000) | A-10 (69.7) | B-6 (159) | 40 | 91.4 |
| 28 | " | " | B-12 (147) | 40 | 90.4 |
| 29 | " | A-8 (78.1) | B-6 (159) | 40 | 96.2 |
| 30 | E-7 (1000) | " | " | 112 | 73.1 |
| 31 | E-1 (1000) | " | B-12 (147) | 40 | 94.8 |
| 32 | E-7 (1000) | " | " | 112 | 73.6 |
| 33 | E-8 (1000) | " | B-1 (147) | 24 | 83.0 |
| 34 | E-6 (6.7) | " | " | 1 | 99.7 |
| 35 | E-4 (66.7) | " | " | 1 | 99.8 |
| 36 | E-6 (6.7) | " | C-5 (153) | 1 | 96.1 |
| 37 | E-4 (66.7) | " | " | 1 | 96.0 |
| 38 | E-6 (6.7) | " | C-18 (227) | 1 | 99.5 |
| 39 | E-4 (66.7) | " | " | 1 | 99.8 |
| 40 | E-6 (6.7) | " | B-12 (147) | 24 | 93.7 |
| 41 | E-4 (66.7) | " | " | 1 | 96.0 |
| 42 | E-6 (6.7) | " | B-6 (159) | 24 | 94.8 |
| 43 | E-4 (66.7) | " | " | 24 | 88.2 |
| 44 | E-1 (1000) | A-1 (100) | B-14 (216) | 1.5 | 93.2 |
| 45 | E-8 (1000) | A-8 (78.1) | C-18 (227) | 48 | 93.1 |
| 46 | E-8 (1000) | " | B-12 (147) | 48 | 86.9 |
| 47 | E-6 (6.7) | A-1 (100) | B-6 (159) | 48 | 72.8 |
| 48 | E-9 (13.3) | A-8 (78.1) | B-8 (138) | 94 | 61.5 |
| 49 | E-9 (13.3) | " | B-1 (146) | 122 | 64.4 |
| 50 | E-6 (6.7) | A-6 (100) | " | 122 | 92.1 |
| 51 | E-6 (6.7) | " | C-18 (227) | 122 | 81.6 |

EXAMPLE 65

A mixture of 10 g of dihydrocholesterol, 11 g of oleic acid, 333 mg (10,000 U) of lipase MY and 5 ml of cyclohexane was stirred at 200 cpm for 64 hours.

The synthesis ratio determined after 40 hours of the reaction was 73.1% and the ratio was 83.1% in 64 hours.

After reaction, the reaction mixture was extracted with aqueous methanol to remove unreacted dihydrocholesterol and oleic acid. Removal of cyclohexane from the cyclohexane layer by distillation gave 12.40 g of desired dihydrocholesterol oleic acid ester.

We claim:

1. A process for preparing a fatty acid ester, the process consisting essentially of reacting:
   (1) a component selected from the group consisting of cholesterol, β-sitosterol, stigmasterol, β-cholesterol, ergosterol, isocholesterol, campesterol, brassicasterol and isotridecyl alcohol and
   (2) a component selected from the group consisting of fatty acids and fatty acid esters,
   in contact with a lipase derived from a microorganism selected from the group consisting of *Candida cylindracea, Pseudomonas fluorescens, Pseudomonas fragi, Chromobacterium viscosum, Aspergillus niger,* and *Rhizopus delemar,* in a reaction system consisting essentially of the component (1), the component (2), the lipase, and either water or a water-containing organic solvent,
   and recovering the product fatty acid ester from the resulting mixture.

2. A process as defined in claim 1 wherein the component (2) is a fatty acid selected from the group consisting of saturated straight-chain fatty acids, saturated branched fatty acids, unsaturated fatty acids, hydroxy fatty acids and polycaroxylic acids having up to 32 carbon atoms.

3. A process as defined in claim 1 wherein the component (2) is a member selected from the group consisting of natural oil, natural fat, synthetic oil, synthetic fat, natural wax and synthetic wax.

4. A process as defined in 1 wherein the component (2) is a glycerin ester of a fatty acid having up to 32 carbon atoms.

5. A process as defined in 1 wherein the component (2) is an ester of aliphatic alcohol having 1 to 14 carbon atoms.

6. A process as defined in 1 wherein the reaction is conducted in a water-containing organic solvent.

7. A process as defined in 1 wherein the water-containing organic solvent is capable of dissolving at least one of component (1) and component (2) and is an organic solvent containing water to at least saturation.

8. A process as defined in claim 7 wherein the water-containing organic solvent is a hydrocarbon solvent saturated with water.

9. A process as defined in claim 7 wherein the water-containing organic solvent comprises the two phases of water and an organic solvent.

10. A process as defined in claim 1 wherein the lipase is separated by phase separation, filtration or centrifugation from the resulting product mixture.

11. A process as defined in claim 1 wherein a porous membrane is used and the component (1) and the component (2) are brought into contact with the lipase through the micropores of the membrane.

12. A process as defined in claim 1 wherein the lipase is used in an immobilized state.

13. A process as defined in claim 12 wherein the immobilized lipase is obtained by an entrapping method using a photo-crosslinkable resin prepolymer or an urethane prepolymer as a carrier.

14. A process as defined in claim 12 wherein the immobilized lipase is obtained by a covalent bond method using an inorganic or organic carrier.

15. A process as defined in claim 12 wherein the immobilized lipase is obtained by an adsorption method using an inorganic or organic carrier.

16. A process for preparing a fatty acid ester, which comprises reacting a component (1) and a component (2) in contact with a cholesterol esterase in a reaction system consisting essentially of said component (1), said component (2), said cholesterol esterase and a water-containing organic solvent, wherein
   component (1) being at least one member selected from the group consisting of cholesterol, isocholesterol, campesterol, stigmasterol, β-sitosterol, brassicasterol, β-cholestanol, 2-octyldodecanol, Lanolin alcohol HH and a branched aliphatic saturated alcohol represented by the following formula:

$$\begin{array}{c}(CH_3)_3CCH_2CH(CH_3)CH_2CH_2 \\ \diagdown \\ \phantom{xxxxxxxxxxxxxx} CHCH_2OH, \text{ and} \\ \diagup \\ (CH_3)_3CCH_2CH(CH_3)\end{array}$$

component (2) being at least one member selected from the group consisting of fatty acids and fatty acid esters in contact with a cholesterol esterase derived from *Candida cylindracea,* and
   recovering the product fatty acid ester from the resulting mixture.

17. A process as defined in claim 16, wherein the water-containing organic solvent is capable of dissolving at least one of component (1) and component (2) and is an organic solvent containing water to saturation.

18. A process as defined in claim 17, wherein the water-containing organic solvent is a hydrocarbon solvent saturated with water.

19. A process as defined in claim 17, wherein the water-containing organic solvent comprises the two phases of water and an organic solvent.

20. A process as defined in claim 11, wherein the component (2) is a fatty acid selected from the group consisting of saturated straight-chain fatty acids, saturated branched fatty acids, unsaturated fatty acids, hydroxy fatty acids and polycarboxylic acids having up to 32 carbon atoms.

21. A process as defined in claim 16, wherein component (2) is a member selected from the group consisting of natural oil, natural fat, synthetic oil, synthetic fat, natural wax and synthetic wax.

22. A process as defined in claim 16, wherein the component (2) is a glycerin ester of fatty acid having up to 32 carbon atoms.

23. A process as defined in claim 16, wherein the component (2) is an ester of aliphatic alcohol having 1 to 14 carbon atoms.

24. A process as defined in claim 16, wherein the cholesterol esterase is separated by phase separation, filtration or centrifugation from the resulting product mixture.

25. A process as defined in claim 16, wherein a porous membrane is used and the component (1) and the component (2) are brought into contact with the cholesterol esterase through the micropores of the membrane.

26. A process as defined in claim 16, wherein the cholesterol esterase is used in an immobilized state.

27. A process as defined in claim 26, wherein the immobilized cholesterol esterase is obtained by an entrapping method using a photo-crosslinkable resin prepolymer or an urethane prepolymer as a carrier.

28. A process as defined in claim 26, wherein the immobilized cholesterol esterase is obtained by a covalent bond method using an inorganic or organic carrier.

29. A process as defined in claim 26, wherein the immobilized cholesterol esterase is obtained by an absorption method using an inorganic or organic carrier.

30. A process for preparing a fatty acid ester, which comprises reacting a component (1) and a component (2) in contact with a cholesterol esterase in a reaction system consisting essentially of said component (1), said component (2), said cholesterol esterase and a water-containing organic solvent, wherein component (1) being at least one member selected from the group consisting of cholesterol, β-sitosterol, isocholesterol, campesterol, stigmasterol, β-sitosterol, brassicasterol, β-cholestanol, 2-octyldodecanol, Lanolin alcohol HH and a branched aliphatic saturated alcohol represented by the following formula:

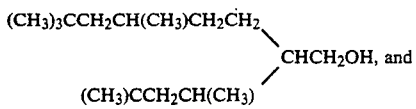

component (2) being at least one member selected from the group consisting of fatty acids and fatty acid esters in contact with cholesterol esterase T-18, and recovering the product fatty acid ester from the resulting mixture.

31. A process as defined in claim 30, wherein the water-containing organic solvent is capable of dissolving at least one of component (1) and component (2) and is an organic solvent containing water to saturation.

32. A process as defined in claim 31, wherein the water-containing organic solvent is a hydrocarbon solvent saturated with water.

33. A process as defined in claim 31, wherein the water-containing organic solvent comprises the two phases of water and an organic solvent.

34. A process as defined in claim 30, wherein the component (2) is a fatty acid selected from the group consisting of saturated straight-chain fatty acids, saturated branched fatty acids, unsaturated fatty acids, hydroxy fatty acids and polycarboxylic acids having up to 32 carbon atoms.

35. A process as defined in claim 30, wherein component (2) is a member selected from the group consisting of natural oil, natural fat, synthetic oil, synthetic fat, natural wax and synthetic wax.

36. A process as defined in claim 30, wherein the component (2) is a glycerin ester of fatty acid having up to 32 carbon atoms.

37. A process as defined in claim 30, wherein the component (2) is an ester of aliphatic alcohol having 1 to 14 carbon atoms.

38. A process as defined in claim 30, wherein the cholesterol esterase is separated by phase separation, filtration or centrifugation from the resulting product mixture.

39. A process as defined in claim 30, wherein a porous membrane is used and the component (1) and the component (2) are brought into contact with the cholesterol esterase through the micropores of the membrane.

40. A process as defined in claim 30, wherein the cholesterol esterase is used in an immobilized state.

41. A process as defined in claim 40, wherein the immobilized cholesterol esterase is obtained by an entrapping method using a photo-crosslinkable resin prepolymer or an urethane prepolymer as a carrier.

42. A process as defined in claim 40, wherein the immobilized cholesterol esterase is obtained by a covalent bond method using an inorganic or organic carrier.

43. A process as defined in claim 40, wherein the immobilized cholesterol esterase is obtained by an absorption method using an inorganic or organic carrier.

44. A process for preparing a fatty acid ester, which comprises reacting a component (1) and a component (2) in contact with a cholesterol esterase in a reaction system consisting essentially of component (1), said component (2), said cholesterol esterase and a water-containing organic solvent, wherein 2-octyldodecanol as a component (1) is reacted with a component (2) selected from the group consisting of capric acid and oleic acid in contact with a panaceas-derived cholesterol esterase, and recovering the product fatty acid ester from the resulting mixture.

45. A process as defined in claim 44, wherein the water-containing organic solvent is capable of dissolving at least one of component (1) and component (2) and is an organic solvent containing water to saturation.

46. A process as defined in claim 45, wherein the water-containing organic solvent is a hydrocarbon solvent saturated with water.

47. A process as defined in claim 45, wherein the water-containing organic solvent comprises the two phases of water and an organic solvent.

48. A process as defined in claim 46, wherein the component (2) is a fatty acid selected from the group consisting of saturated straight-chain fatty acids, saturated branched fatty acids, unsaturated fatty acids, hydroxy fatty acids and polycarboxylic acids having up to 32 carbon atoms.

49. A process as defined in claim 46, wherein component (2) is a member selected from the group consisting of natural oil, natural fat, synthetic oil, synthetic fat, natural wax and synthetic wax.

50. A process as defined in claim 46, wherein the component (2) is a glycerin ester of a fatty acid having up to 32 carbon atoms.

51. A process as defined in claim 46, wherein the component (2) is an ester of aliphatic alcohol having 1 to 14 carbon atoms.

52. A process as defined in claim 46, wherein the cholesterol esterase is separated by phase separation, filtration or centrifugation from the resulting product mixture.

53. A process as defined in claim 46, wherein a porous membrane is used and the component (1) and the component (2) are brought into contact with the cholesterol esterase through the micropores of the membrane.

54. A process as defined in claim 46, where the cholesterol esterase is used in an immobilized state.

55. A process as defined in claim 54, wherein the immobilized cholesterol esterase is obtained by an entrapping method using a photo-crosslinkable resin prepolymer or an urethane prepolymer as a carrier.

56. A process as defined in claim 54, wherein the immobilized cholesterol esterase is obtained by a covalent bond method using an inorganic or organic carrier.

57. A process as defined in claim 54, wherein the immobilized cholesterol esterase is obtained by an absorption method using an inorganic or organic carrier.

* * * * *